(12) United States Patent
Varma et al.

(10) Patent No.: US 8,791,044 B2
(45) Date of Patent: Jul. 29, 2014

(54) DOPED TITANIUM DIOXIDE AS A VISIBLE AND SUN LIGHT PHOTO CATALYST

(75) Inventors: Rajender S. Varma, Cincinnati, OH (US); Babita Baruwati, Bangalore (IN); Jurate Virkutyte, Cincinnati, OH (US)

(73) Assignee: The United States of America as Represented by the Administrator of the U.S. Environmental Protection Agency, Washington, DC (US)

( * ) Notice: Subject to any disclaimer, the term of this patent is extended or adjusted under 35 U.S.C. 154(b) by 0 days.

(21) Appl. No.: 12/662,742

(22) Filed: Apr. 30, 2010

(65) Prior Publication Data

US 2011/0266136 A1 Nov. 3, 2011

(51) Int. Cl.
*B01J 23/00* (2006.01)
*C01G 23/047* (2006.01)
*C23C 16/40* (2006.01)

(52) U.S. Cl.
USPC ........... 502/350; 423/610; 423/611; 423/612; 423/613; 423/614; 423/615; 423/616; 106/287.19

(58) Field of Classification Search
USPC .............. 502/350; 423/610–616; 106/287.19
See application file for complete search history.

(56) References Cited

U.S. PATENT DOCUMENTS

| | | | | |
|---|---|---|---|---|
| 5,547,655 | A * | 8/1996 | Chou et al. ................. | 204/157.4 |
| 6,489,433 | B2 * | 12/2002 | Duan et al. .................... | 502/150 |
| 7,976,909 | B2 * | 7/2011 | Durandeau et al. ........... | 427/576 |
| 2008/0031832 | A1 * | 2/2008 | Wakefield et al. .............. | 424/59 |
| 2009/0005238 | A1 * | 1/2009 | Falaras .......................... | 502/200 |
| 2010/0190643 | A1 * | 7/2010 | Hugener-Campbell et al. ............................. | 502/350 |
| 2011/0124492 | A1 * | 5/2011 | Loukine et al. ............... | 502/159 |

FOREIGN PATENT DOCUMENTS

JP 2005-139020 * 6/2005

OTHER PUBLICATIONS

"Preparation and characterization of nano silver-doped mesoporous titania photocatalysts for dye degradation," N. N. Binitha et al. Catalysis Today 1475 (2009), pp. 576-580.*
"A simple method to prepare N-doped titania hollow spheres with high photocatalytic activity under visible light," Yanhui Ao et al. Journal of Hazardous Materials 167 (2009), pp. 413-417.*
"Effect of thermal treating temperature on characteristics of silver-doped titania," Chai Li-yuan et al. Trans. Nonferrous Met. Soc. China 18 (2008), pp. 980-985.*
"Photocatalytic degradation of cyanide using titanium dioxided modified with copper oxide," K. Chiang et al. Advances in Environmental Research 6 (2002), pp. 471-485.*
"A visible light response TiO2 photocatalyst realized by cationic S-doping and its application for phenol degradation," Shouxin Liu et al. Journal of Hazardous Materials 152 (2008), pp. 48-55.*
"Visible-light-induced degradation of formaldehyde over titania photocatalyst co-doped with nitrogen and nickel," Xin Zhang et al. Applied Surface Science 254 (2008), pp. 4780-4785.*

\* cited by examiner

*Primary Examiner* — Patricia L Hailey
(74) *Attorney, Agent, or Firm* — Hendricks & Assoc.

(57) ABSTRACT

Methods for preparing and using a photocatalyst are described. The catalyst is prepared by oxidation of a metal salt which has been doped in situ to form a photocatalyst active in visible light. The photocatalyst is used for degrading toxic and irritating compounds and infectious agents.

20 Claims, 11 Drawing Sheets

DOPED TITANIUM DIOXIDE AS A VISIBLE AND SUN LIGHT PHOTO CATALYST

FIELD OF THE INVENTION

The present invention relates to catalyst compositions and methods for preparing and using them for photocatalyzing organic compounds.

BACKGROUND OF INVENTION

In recent years, it has been recognized that both chemical synthesis and chemical degradation are preferably performed using technologies that are more sustainable, less hazardous, less polluting and with less byproduct waste. Among other technologies, photocatalysts have been recognized as desirable.

Over the years many have attempted and considerable effort has been applied to develop photocatalysts which can act as self-cleaning coatings, anti-microbial coatings and surfaces degrading organic contaminants, particularly those not readily biodegradable. Titanium dioxide ($TiO_2$) has been of particular interest due to its low cost, almost no toxicity, chemical stability (both to light and the environment) and high photoactivity.

$TiO_2$ is a semiconductor with a number of properties pertinent to photocatalysis such as transparency to visible light, high refractive index and low absorption coefficient. $TiO_2$ has been used in a wide range of applications including ultraviolet filters for optics and packing materials, environmental remediation, papermaking, ceramics, solar cells, electrochromic displays, anodes for ion batteries, self-cleaning coatings and paints and humidity as well as gas sensors.

A large number of prior state of the art references have mentioned using titanium dioxide as a photocatalyst for an assortment of chemical reactions and antimicrobial activity. Many attempts have been made to modify the photocatalytic activity by doping the titanium dioxide with a number of different compounds and using a number of different techniques. Several different nitrogen-containing compounds have been tried using a variety of different doping reactions. However, these attempts have limited stability and efficiency or were active only or primarily under UV light.

Of particular interest has been the rutile and anatase crystalline phases of $TiO_2$. $TiO_2$ has been used extensively under ultraviolet irradiation (UV) due to its large band gap of 3.2 eV. $TiO_2$ exhibits high reactivity and chemical stability under ultraviolet (UV) irradiation at wavelength 387 nm, whose energy exceeds the band gap of 3.0 eV and 3.2 eV for rutile and anatase crystalline phase, respectively. (Asahi et al, Science 293, 269 (2001) and Jagadale et al, J. Phys. Chem. C, 2008, 112, 14595.)

Due to the size of its band gap, pristine $TiO_2$ is active only under UV irradiation, which comprises less than 5% of solar light energy. While functional under UV irradiation, photocatalysis generally does not occur in indoor areas under conventional artificial light or even ambient daylight as UV is not present.

A number of attempts have been made to modify $TiO_2$ to enhance its activity by doping the crystalline structure with a variety of compounds including those with nitrogen, carbon or sulfur atoms. Some attempts have been made to obtain visible light activation of the photocatalysts by the red shift of the adsorption spectrum. Nitrogen atoms have attracted the most attention because its p state contributes to the band gap narrowing by mixing with the oxygen 2p states. (Asahi et al, Science 293: 269 (2001).) Nitrogen doping has been performed by using nitrogen gas, ammonium chloride, ammonia gas and a number of nitrogen containing organic compounds.

Other compounds including noble metals and non-metal species deposited on $TiO_2$ may show different effects on the photocatalytic activity of $TiO_2$ under solar and artificial visible light irradiation. (Kisch et al, Angew. Chem., Int. Ed., 37: 3034 (1998). According to Sung-Suh et al, J. Photochem. Photobiol. A—Chem. 163: 37 (2004)) There are several mechanisms that are responsible for such effects: i) dopants enhance the electron-hole separation by acting as electron traps, ii) they extend the light absorption into the visible range and iii) e.g. noble metals modify the surface properties of the photocatalyst. Metal dopants affect the surface properties by generating a Schottky barrier of the metal in contact with $TiO_2$ surface, which acts as an electron trap and inhibits $e^-$-$h^+$ recombination (Zhou et al, Ind. Eng. Chem. Res., 45: 3503 (2006)). Silver is a metal that is suitable for numerous industrial applications. It has been reported that silver deposited onto $TiO_2$ significantly shortens illumination period and increases the efficiency of the catalyst (Soökmen et al, J. Photochem. Photobiol. A—Chem., 147: 77 (2002)).

A number of different metals, especially transition metals, when used as dopants, cause the titanium dioxide to increase adsorption of visible light. Unfortunately, many of these result in a reduction of photocatalytic activity in the UV range and also are not sufficiently stable to prevent rapid loss of photocatalytic activity of the catalyst.

Nitrogen-doping has been effective in decreasing the band gap of $TiO_2$ through mixing of N 2p and O 2p states due to the electronic transitions from the dopant 2p or 3p orbitals to Ti 3d orbitals (Fu et al, J. Phys. Chem. B, 110, 3061. (2006)). Such doping is also attractive because of comparable atomic size of nitrogen with oxygen, small ionization energy, metastable center formation, and remarkable stability (Jagadale et al., J. Phys. Chem. C, 112, 14595 (2008)).

References mentioning doped titanium dioxide photocatalysts that show any photocatalytic activity under visible light conditions are Sakthivel et al, Angew. Chem. Int. ed. 42: 4908 (2003), Matsushita et al, Journal of the Ceramic Society of Japan, Supplement 112-1, PacRim5 Special Issue, 112[5] S1411 (2004) and Nosaka et al, Science and Technology of Advanced Materials, 6: 143 (2005).

There is a lack of studies utilizing 'green' nanoscience principles to fabricate noble metal and non-metal co-doped $TiO_2$ catalysts utilizing renewable sources or various waste materials) Hamal et al, J. Coll. Interf. Sci, 311, 514 (2007)). Also, there is a lack of proven photocatalytic effectiveness using ambient light, particularly in poorly illuminated areas. It was to address the problems indicted above that the present invention was pursued.

SUMMARY OF THE INVENTION

The goal of the present invention is to provide a means for degrading pollutants in gases, liquids and on surfaces by contact with a photocatalyst. The photocatalyst was prepared in an environmentally friendly manner from relatively non-toxic materials which come from renewable sources and wastes, functioned in ambient conditions, and proved recyclable.

The present invention provides for the fabrication of doped $TiO_2$ photocatalysts with high stability and reactivity under artificial visible and solar light (wavelength>380 nm). This allows the photocatalyst to utilize a greater portion of the solar spectrum and be active during daylight and/or ambient or illuminated indoor areas.

In the present invention the photocatalyst is used to completely or at least partially degrade organic compounds in gasses, liquids or solids contacting the photocatalyst under visible light.

The present invention also provides for a titanium dioxide photocatalyst which is doped with two different dopants, preferably a metal and a non-metal.

The present invention also further provides for the use of organic or silicon containing polymeric dopants in forming the photocatalyst.

The present invention further provides for a photocatalyst containing doped $TiO_2$ where the titanium dioxide is entirely or nearly entirely in the anatase phase except, perhaps, for trace amounts of rutile phase.

The present invention provides for a photocatalyst synthesis method using an in-situ sol-gel synthesis of doped titanium dioxide utilizing mild reaction conditions and benign precursors and avoiding organic solvents.

The present invention also provides for a photocatalyst synthesis method using an in-situ sol-gel synthesis of doped titanium dioxide from non-oxides of titanium mixed with the dopant.

While techniques are known for making $TiO_2$ based photocatalysts and other techniques are known for doping titanium dioxide, these techniques generally start with commercially available preformed $TiO_2$. Sol-gel synthesis techniques are known but for forming different materials. However, the present invention uses an in-situ sol-gel synthesis with dopant(s) to form a doped $TiO_2$ photocatalyst active under visible light.

The present invention involves methods using nitrogen, silver, bismuth, copper, sulfur, carbon and oxygen containing compound(s). These used in conjunction with the synthesis methods results in a photocatalyst activated by visible light.

The present invention still further may use multiple dopant compounds that come from organic and inorganic sources simultaneously. These combinations display greater activity and have high synergistic index than any of the individual dopants used alone.

It is a feature of the present invention for the photocatalyst to be stable and recyclable many times while maintaining photocatalytic activity under visible light. While the present invention is discussed in terms of degrading organic compounds, the compositions and methods of the present invention may be applied to synthesis of desirable compounds from starting compounds and to catalyzing reactions with inorganic compounds.

DETAILED DESCRIPTION OF THE INVENTION

Figure 1:
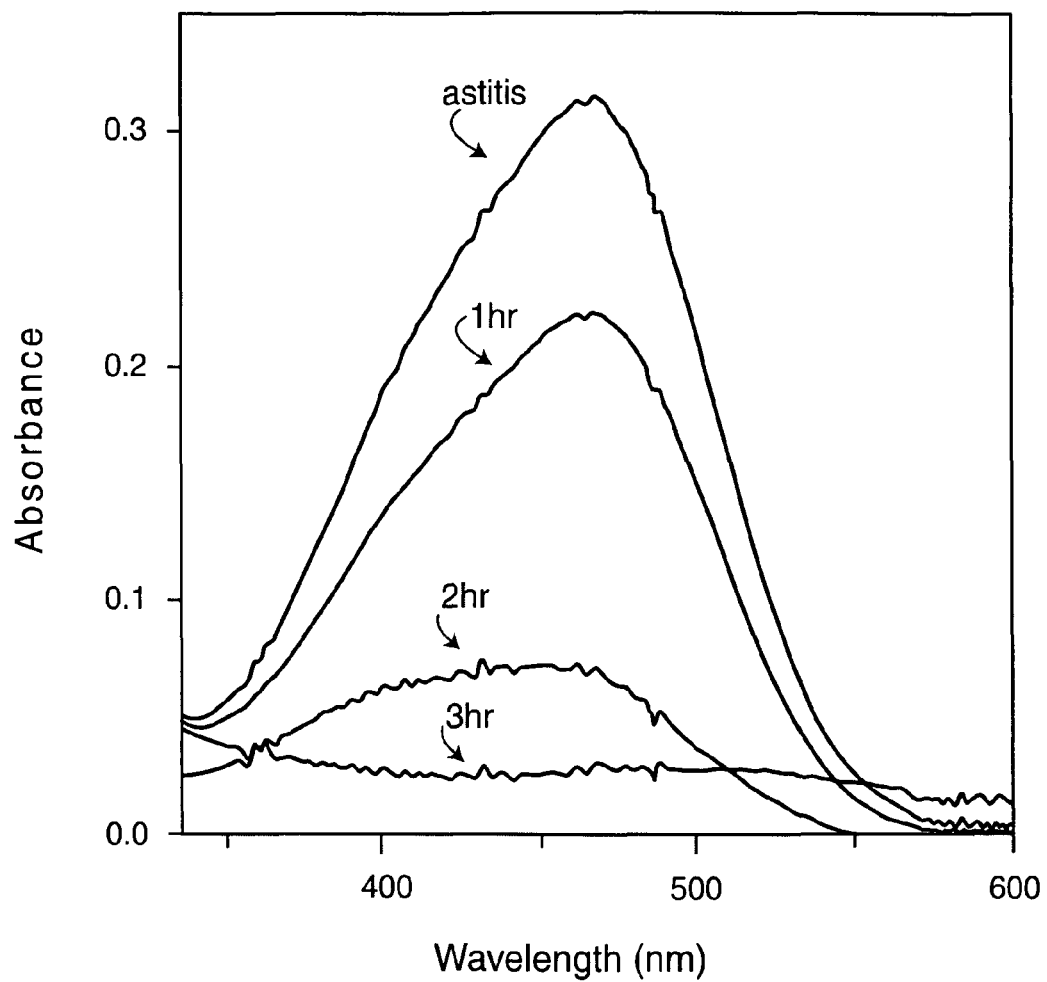
FIG. 1 is a UV plot for the degradation of methyl orange with time using the catalyst Ti350. A 3 g/l of catalyst was used.

While not wishing to be bound by any particular theory as to how the catalyst is formed or the present invention operates, several proposed mechanisms for both the synthesis and reactions using the catalyst are presented. These are provided to give a better understanding of the mechanisms and the reasons why related catalysts would be expected to function even though they are not exemplified.

A first preferred embodiment of the present invention is the general method to synthesize catalysts of the present invention. In this general method, a water soluble (preferably in acidic conditions) titanium salt is mixed with a doping material followed by hydrolysis of the titanium salt to form an insoluble substance which is then calcined at a temperature and for a time sufficient to form a doped titanium oxide. The resulting material is then used as a catalyst.

While exemplified by use of titanium as the metal salt starting material, other metals may be used alone or in combination with each other to eventually form the solid oxides of the metals. Metals oxides which may be substituted for titanium include: zinc, cerium, indium, tin, aluminum, and silicon. Among these, Zn, Ti, Ce, In, and Sn may result in oxide crystals having an light absorption favorable for photocatalysis.

Multiple metals forming an oxide may also be used. These may include titanium or not. Examples of the resulting oxide include: $ZnIn_2O_4$, $Zn_2In_2O_5$, $Zn_3In_2O_6$, $GaInO_3$, $In_4Sn_3O_{12}$, $Zn_2SnO_4$, and $ZnSnO_3$, $ZnAl_2O_4$, $Zn_2B_6O_{11}$, $ZnFe_2O_2$, $ZnMoO_4$, $ZnSeO_3$, $Zn_2SiO_4$, and $ZnWO_4$. Al, Cr, Mg and Ca also prepare suitable oxides for using alone or in combination with other metals. Cu, Ag, Ti, Mn, and Bi may also be used alone or in combination with Al, In, Sn, Fe, Co, Ce, Ga, Ni, Mn, Zr, Ag, alkaline metal elements, and alkaline earth metal elements or these may be used alone.

The choices for non-metal in the initial salts is very broad. The non-metal may be inorganic or organic and serves as the cation(s) for titanium or other metal ions. The resulting salt is used as a starting material and should be soluble. The desirable trait is for it to be removed when titanium or other metal ions are reacted to form an insoluble salt. As a typical agent to insolubilize titanium salts, hydroxides are used and are allowed to react to form titanium hydroxide and the remaining non-metal from the initial salt is preferably dissolved in the liquid. Representative examples of the non-metal anions include halogens, nitrogen, etc.

When it is desirous to add a doping agent at least partially composed of the non-metal, one can be simultaneously synthesized from the non-metal of the initial titanium salt. For example, when it is desirable to incorporate sulfur into the resulting titanium dioxide solid, one can start with titanium sulfide, sulfate or sesquisulfate in dilute sulfuric acid. One then adds calcium hydroxide or barium hydroxide to simultaneously form titanium hydroxide and an insoluble calcium sulfate or barium sulfate. When the solid, sol, gel or precipitate is dried and calcined, the sulfur (or other atoms) is retained in the titanium dioxide matrix to provide the doped titanium dioxide catalyst. A similar result may occur by doping with fluorine, which may be provided by starting with titanium fluoride instead of chloride.

Precipitates may be formed by other means such as initially reacting the strong reducing agent titanium sulfate with an oxidizing agent.

Dopants may also be added separately to the metal salts before insolubilization so as to incorporate the dopant into the insoluble particles. After calcination, the dopant (or some of the atoms from the &pant) is then found in the titanium dioxide particle. Calcination may remove part or all of the components of the dopant. This process aids in making the titanium dioxide more porous, a desirable trait, as greater surface area provides for greater catalytic activity. Dopants may be either organic or inorganic compounds or mixtures thereof.

Dopants may constitute a very small part of the resulting titanium dioxide crystal structure but are intentional additions. Compositions added as dopants may contain low concentrations of the active doping ingredient but they are not unintentional trace amounts. Trace contaminants in unwanted small amounts found in various reagents do not constitute a dopant for the purpose of the present invention unless they are specifically desired to be added.

Preferred examples of beneficial dopants include nitrogen containing compounds, organic or inorganic sulfur containing compounds, silver containing compounds, and various polymers. The choice is among those capable of producing n-doped titanium dioxide. Those that can split the electron hole pairs by attracting conduction band photoelectrons are particularly preferred. While the number of suitable dopant compounds is large, compounds rich in such elements are preferred. For example, for nitrogen containing compounds, guanidine and melamine are exemplified below. Other compounds such as urea may also be suitable. Dopants containing two or more of the desired dopant components are also a preferred class. For example thiourea provides both N and S.

Certain inorganic compounds may also provide a suitable dopant. Of particular interest are those containing metals that have antimicrobial activity such as silver, copper and bismuth. Non-metals may be used also such as such as inorganic sulfur compounds. Toxic inorganics, such as those containing chromium or arsenic, may be used but are generally too toxic for many of the applications of the present invention.

Polymer dopants may be essentially pure substances, such as microcrystalline cellulose used in Example 15 below or may be a mixture such as garlic used in Example 12 below. A polymer dopant may be used in conjunction with a single compound dopant. Other representative dopants include polysaccharides, (cellulose, starches, dextrins, chitin, alginates etc.), polyesters (including polynucleic acids), polythiophene, polyamides (including proteins such as gelatin, collagen, albumin and mixed proteins), polyurethanes, siloxanes, polyolefins (including halogenated and other substituted forms), polynitrile, graphite, etc. The polymer may be a homopolymer or copolymer of defined, block or random composition.

The dopant need not be a separately added composition but may be provided in situ. For example, when titanium (or other metal) salts contain nitrogen in either the cation or the anion form that is insolubilized and ends up in the resulting catalyst product, then the same doping result may be achieved without adding a separate compound.

The insolubilized doped material is changed into a catalytically active crystalline material. Typically this is done by heat treatment, but other forms of oxidation may be used. During heat treatment or calcination with a doped titanium hydroxide material, the oxide is formed and simultaneously doped titanium dioxide crystals are formed.

When doping $TiO_2$ it is preferable to use a non-metal in conjunction with the use of a metal. The two dopants function cooperatively to exhibit more beneficial effects on the catalyst as compared with sole non-metallic or metalic dopant. In the present invention, a one-pot facile synthesis of $TiO_2$ nanoparticles co-doped with for example, guanidine nitrate and silver nitrate, is used to increase their photocatalytic activity in the visible light range. Other combinations of plural dopants may be used.

A single dopant may be employed which functions as plural dopants. For example, a single composition may be added to provide sulfur and nitrogen. In the final composition after calcinations, it is important that the desired atoms are present in the desired configuration. This may not entirely depend on the details of the dopant(s).

The time and temperature conditions during calcining are important as the use of higher temperature and/or longer calcining times increases the formation of rultile $TiO_2$. This is undesireable in practicing the present invention as it is the anatase phase of $TiO_2$ that has superior photocatalytic activity in visible light. However a minimal temperature/time is needed to fully oxidize the titanium and dopant and to remove any free water and oxidation products. This is typically observed in a thermal degradation experiment where the pattern, thermogravimetric spectra or curve is measured. When the reduction in weight is complete, the oxidation during calcination is essentially finished. For example, see FIG. 4a or FIG. 11.

Also, the temperature and time of calcination affects the size and agglomeration of crystalline particles. See FIG. 3. In the present invention, it is desirable to have a very porous product to have a high surface area for catalysis.

The amount of calcination also affects the composition of the dopant and its interaction with the $TiO_2$. Oxidation and degradation of the dopant and reaction with, formation of, and porosity of titanium dioxide are examples of properties affected by the calcination.

In the present invention, the best calcination conditions to use will vary with the particular catalyst being formed. For doped titanium dioxide catalysts in the present invention, a temperature and duration sufficient to produce an anatase phase titanium dioxide with minimal amounts of rutile or brooklite phases is preferred. The essentially pure anatase phase as determined by X-ray diffraction. There are no strict limits as a mixture may still provide a useful but lesser amount of catalytic activity. For example 2 hours at 350 degrees C. is adequate in Example 2 below but the same composition calcined for 550 degrees C. for 6 hours would result in some rutile phase being formed and/or in overly large crystals with a lower surface area and/or a greater agglomeration with less porosity being formed, resulting in lower photocatalytic activity.

For doped titanium dioxide catalysts, the anatase phase should be in far excess of other phases. Generally at least a 10:1 ratio should be present with greater than 100:1 being preferred.

However, with different dopants or combinations of dopants, longer and higher temperature calcination reactions may be preferred, as shown in Table 1 below. In this situation, calcination was needed to proceed until the preferred crystal size was achieved.

The combinations of calcination times and temperatures used will vary somewhat among exact compositions. Preferred combinations may be empirically determined and can vary even for the same composition. For example, a longer duration may compensate for a lower temperature and vice versa. In each situation, the photocatalytic activity determines the desirable conditions.

During fabrication of the visible-light photocatalytic composition, the activity of novel $Ag/TiO_{2-x}N_x$ or other composition photocatalyst is preferably high in visible light. Facile and simple synthesis of the invention's $Ag/TiO_{2-x}N_x$ catalyst under mild experimental conditions produced remarkably efficient, stable, recyclable and active photocatalyst functional under visible light.

The simple and facile synthesis of the photocatalysts of the present invention demonstrated the applicability of the selected precursors and synthesis protocol for the fabrication of extremely active, stable and reusable photocatalyst that is active in the visible light range. Furthermore, when Ag is in the doped $TiO_2$ composite materials antimicrobial activity is presumed to be enhanced further, since silver ions alone are well known antimicrobial agents. This composition in particular is preferred for the elimination of microbial and chemical contamination simultaneously.

As heterogeneous photocatalysis is a surface process, surface modification with silver particles and nitrogen significantly alter surface characteristics, which results in the change in surface area exposed to the light. In general, these catalysts fabricated under the mild conditions of the present invention using benign precursors are desirable, since an important part of the present invention is that the i) catalyst was not poisoned by various impurities such as reaction intermediates and was shown active for at least 5 consecutive runs without a significant loss in activity and ii) theormogravimetric analysis showed excellent thermal stability.

Another preferred embodiment of the present invention is to use the catalysts produced. These catalysts have many uses in industry. Of particular interest are those photocatalysts active under visible light.

The photocatalysts of the present invention can catalytically react with organic compounds to effect their degradation. It is of particular value to use the present invention to kill microorganisms, to degrade allergens and to degrade toxic compounds. The catalysts may also be used to catalyze various chemical reactions, thereby producing a large number of desired chemicals.

The desired reactions of the invention may occur in a gases, liquids or on the surface of solids. The photocatalysts of the present invention may be used alone or bound to the surface of a solid to immobilize the catalyst. Examples of their use in a gaseous environment are to coat fan blades, air filters, a porous bed or fluidized bed of particles to kill microorganisms in the air and other areas (preferably with a high surface area) where air passes by the photocatalyst. This would have use in clinical, industrial, and military settings as well as for residential indoor air. The photocatalyst may be adhered to a solid phase electrostatically or with a binder. The catalyst may be used alone, be suspended in or pass through the gas being treated. Solids are recovered by settling, filtration, centrifugation (e.g. cyclone) etc. and the photocatalysts reused.

Nearby ambient or artificial light may be provided to facilitate the desired action. Representative use examples are to degrade hydrocarbons found in indoor (or inside an enclosed area such as a vehicle) air caused by smoke or other air pollutants, inactivation of allergens and pathogens, inactivation of toxins or irritants from either indoor or outdoor air. The compounds being catalyzed may be volatile or aerosol. A particularly desirable feature of the catalysts of the present invention is that they would be highly economical for outdoor applications related to the degradation of organic pollutants.

Examples of uses in liquid environments include use in filters, on surfaces contacting fluid flows, and immobilized on floating, sinking or suspending solids (particularly if the photocatalyst does not naturally have such a property). The catalyst may be used by itself and optionally be recovered by settling, flocculation, filtration, centrifugation (e.g. hydroclone) etc. and reused.

Nearby ambient or artificial light may be provided. Other examples of use are to degrade pollutants found in wastewater, water from polluted sites or naturally toxic sites (e.g. tailings, mines, leached water) to remove pathogens, toxins and irritants in water for drinking, for agricultural use, for industrial use, or for release into the environment. A particularly desirable feature of the catalysts of the present invention is that it would be highly economical for outdoor applications related to the degradation of organic pollutants.

Examples of uses on solid surfaces include applying the catalyst, preferably mixed in a liquid for ease of application, to a solid surface where one wishes to affect the solid surface or materials on the solid surface. The solid surface can be of any size and configuration including dust particles and fuel storage tanks. The catalyst may be permanently bonded to the solid surface or another mobile solid surface. The catalyst may be recovered by vacuuming, washing, etc. or may remain on the solid surface to produce a continual catalytic surface for self cleaning and the like.

Nearby ambient or artificial light may be provided. Other examples of application are to disinfect surfaces, clean up releases of toxins or pollutants from leaks and spills, or intentionally contaminations. The catalysts may be used prophylacticly for protection from the same sources of contamination. Specific examples of sites for application include door knobs, fuel tanks and handling equipment, children's toys, table surfaces, walls, preservative treated lumber, military equipment, medical equipment, food processing surfaces, and on equipment used with or nearby toxic chemicals such as in agricultural, industrial and medical environments.

The photocatalysts of the present invention may be utilized in a reaction chamber where the fluids or solids being treated are transported through the reaction chamber. This may be useful for treating harmful waste and for sterilizing and decomtaminating fluids for human use. Even laundry and other washing may incorporate the photocatalysts of the present invention. Swimming pool surfaces or a reaction chamber exterior to the pool for which water us pumped through may contain the photocatalyst.

The photocatalysts in presence of ambient or artificial light may be used as a substitute for all applications which required UV light treatment, particularly sterilizations and chemical reactions.

The photocatalyst may be mixed in a liquid containing a thickener or adhering agent to bind it to a solid surface. For example, a paint or other coating on objects exposed to ambient light. It may be used as a coating on a fuel container, pesticide container or other toxic chemical container to self clean any small leaks, spills, drips or aerosol contaminations. Likewise food containers may be so coated to prevent microbial growth near the food product. Also, a coating of the present invention may be applied to surfaces exposed to environmental microbes or larger plants and animals and toxins such as exposed man-made structures. Sewage treatment equipment, hulls of ships, underwater equipment, support structures etc. typically become fouled by microbes, barnacles, etc. A coating of the catalyst of the present invention may reduce this fouling.

The photocatalysts may also be bound to inert small particles for ease of handling and manipulation, particularly with respect to a light source. The particles may be charged or magnetically responsive permitting ease of movement when suspended in fluids or on solids. It is possible to recover the photocatalyst by application of various electrical or magnetic fields.

The photocatalysts of the present invention may also be used for medical and cosmetic uses, including as a disinfectant, skin treatment, etc. Because of their relative inertness, the photocatalysts may be administered internally to a patient with a optical fiber applying light to the particular site where photocatalytic activity is desired, such as at a blood clot or at a tumor site. The photocatalyst may be applied during surgery to reduce infection and degrade clots.

The photocatalytic activity of the catalyst may be measured by many methods. In the present invention, the catalyst was characterized and used for the decomposition of methyl orange, 2,4 dichlorophenol and methylene blue as model reactions. These compounds are recognized as pollutants. For example, methyl orange (MO) is a highly toxic, complex and non-biodegradable azo dye, which is classified as a micropollutant and is widely used in the textile industry. As such, it is a model pollutant to evaluate the photocatalytic activity of as-prepared nanocatalysts in the visible light range.

The present invention encompasses using the catalytic activity of the catalyst to degrade a large number of different organic chemicals. Likewise, the catalytic activity can synthesize a desirable chemical from a precursor chemical. The present invention also be used for catalyzing chemical reactions for inorganic compounds.

Another preferred embodiment of the present invention is catalyst itself. The photocatalyst is highly porous having a BET surface area of greater than about 150, preferably >200 $m^2$/gram. A photocatalysts of the present invention are titanium dioxides with essentially all of it in the anatase phase other than traces of rutile and/or brookite phases. Residual traces of non-oxides of titanium salts, such as TiS2, may also be present. In general the ratio of anatase to rutile phases is greater than 10:1

Where two or more metals are present or two or more non-metals are present in the crystal, the phases may altered as to the preferred crystal size. However, both of these are affected by the calcination time and temperature and the optimum may be empirically determined by trial and error for each catalyst.

The individual doped catalyst crystals are generally less than 30 nm, preferably 5 to about 20 nm, more preferably 10-20 nm. The form may also be referred to as nanocrystals. The nanocrystals are frequently agglomerated in to larger sized particle.

While measuring catalytic activity may be the most preferred method for analyzing the catalysts of the present invention, when one does not know the final use for the catalyst, the choice of test reagent conditions is difficult. One way to infer photocatalytic activity of photocatalysts of the present invention is to measure absorbance at a number of wavelengths in the visible (and, optionally, in the UV) range to determine the catalyst's optical absorbance at the differing wavelengths. Catalysts absorbing light in the visible range are believed to offer greater potentially photocatalytic activity in that range.

For dopants using hybrid inorganic/organic materials, the resulting catalyst constitutes a new class of functional nanocomposites that exhibit enhanced optical, thermal and mechanical properties due to the synergistic effects resulting from the physical and chemical interactions that occur between the components.

This result, combined with benign starting materials and a facile in situ sol-gel synthesis of $TiO_2$-based nanocomposite is a simple and effective way to photocatalyze a number of compounds in a variety of situations. It should be noted that utilizing inexpensive and benign materials, such as microcrystalline cellulose, garlic (in the aqueous phase and under mild reaction conditions) produce relatively little in the way of toxic byproducts or chemical waste. Likewise titanium dioxide, and, presumable, the related doped products, appear to be very benign. The overall method is easy to implement and relatively cheap, in keeping with the green chemistry principles, by avoiding the use of organic solvents and high temperatures.

Another embodiment of the present invention is a photocatalyst of the present invention that is both recyclable and, when fouled, can be regenerated. The doped nanocrystalline $TiO_2$ exhibits photocatalytic activity in the visible light range and can decompose various organic pollutants. The reactions using the catalysts of the invention worked even under common household lightbulbs, as well as in sunlight. Reuse of the catalyst five times did not result in any loss of its efficiency. Even after repeated usage and a noticeable reduction in activity, the catalyst may be regenerated simply by washing with water. For better use, the catalyst may then be dried with a solvent, such as acetone and/or by drying at temperatures below the calcining temperature so as to not affect the phase of titanium dioxide.

It is of particular importance to the present invention to facilitate the synergetic effects of multiple dopants on the crystallinity, surface area and porosity, thermal stability and surface reactions as well as photocatalytic activity of $TiO_2$ or other metal oxides. The use of organic sulfur compounds from garlic (*Allium sativu*), onions, eggs, other organic sulfur compounds, etc. in combination with silver ions to dope nano-$TiO_2$ to increase its activity resulted in very high degrading activity against model organic compound pollutants.

In this embodiment of the present invention, simultaneous doping of $TiO_2$ with *Allium sativum* and silver ions was practiced via facile sol-gel process, using benign and renewable precursors, which resulted in a significant improvement in the photocatalytic activity of the catalyst compared to the commercially available Degussa P25 catalyst for use in the visible light range. Also, the effect of calcination temperature on photocatalytic activity was shown to affect the resulting activity.

It is recognized that plant, animal and microbial products are typically complex mixtures. Yet, effective catalysts can be prepared for wide using the same as doping agents.

While applicants do not wish to be bound by present theories, a discussion of the theory behind the catalysis may help explain the functioning and why the results obtained are expected to be broadly applicable.

The energy of a single photon can be calculated by using Planck-Enstein equation $$E = \frac{hc}{\lambda}$$

where E is the energy of a single photon (W s), h is the Planck's constant ($6.626 \times 10^{-34}$ J s), c is the speed of light $(2.998 \times 10^8 \text{ m s}^{-1})$ and $\lambda$ is the wavelength of the irradiation source (nm). Total power absorbed is calculated:

$$P = F_a \times \text{lamp power} \times t$$

where $F_a$ is fraction of absorbed light, lamp power is indicated by the manufacturer (300 W) and t is the irradiation time. Number of [MO⁻] molecules decomposed:

$$N_{[MO^-]} = \frac{d[MO^-]}{t} \times N_A$$

where $d[MO^-]_d/t$ is degraded MO in the aqueous solution over a period of time (mol) and $N_A$ is Avogadro constant $(6.022 \times 10^{23} \text{ mol}^{-1})$. Number of photons absorbed:

$$N_p = \frac{P}{E}$$

Quantum efficiency is then calculated accordingly:

$$Q_e = \frac{N_{[MO^-]}}{N_p}$$

As quantum efficiency depends on various parameters above, it is crucially important to take into account various reaction conditions to increase the $Q_e$ in order to enhance the overall degradation process efficiency. For instance, if we assume that 100% of light is absorbed and no light is reflected from the surface, $Q_e$ of catalysts range from 1.5 to 19%. However, if the absorbance is less (e.g. 30% according to our previous research on N-doped $TiO_2$ data) under the same reaction conditions, the quantum efficiencies demonstrate nearly 3-fold increase and range from 5.1 to 57%.

In addition, it is generally accepted that incandescent light bulbs emits 10% of energy as visible light and the rest is attributed to the heat. Thus, in order to have an economically feasible and attractive degradation process, one needs to either use more efficient light source or utilize abundant solar light.

Photocatalytic Mechanism:

The surface of $TiO_2$ consists of rows of Ti atoms, in-plane oxygen atoms and bridging oxygen atoms. Dopants may distort the lattice and substitute for either $O^{2-}$ or $Ti^{4+}$. Depending on the calcination temperature, sulfur and other atoms can be absorbed onto $TiO_2$ or substitute either $Ti^{4+}$ or $O^{2-}$.

The photocatalytic degradation is a very complicated process, which is affected by the crystallinity, crystallite size, phase/chemical composition of the catalysts and the morphology of particles.

It is assumed that produced radicals ($.O_2^-$, $.OH$, etc) are the major species responsible for the photocatalytic degradation of organic contaminants. The hole in the VB can be captured by $OH^-$ or $H_2O$ species adsorbed on the surface of the catalyst to produce radicals, whereas photogenerated electrons in the CB can reduce the adsorbed oxygen into $.O_2^-$, which contribute to the increased activity of the nanocatalyst. In addition, hole itself can also effectively oxidize target pollutants adsorbed onto the surface of the catalyst. Apparently, the degradation of model pollutants proceeded on the surface of the nanocatalyst by the synergistic effect of holes and produced radicals, and not in the bulk of the solution due to the fact that photogenerated radicals were extremely short lived and tended to recombine to form water. In addition, the occurrence of anatase phase with high degree of crystallinity and slightly distorted lattice by the introduced dopants enhanced the photocatalytic degradation of the model pollutant in the liquid phase.

In addition to the photocatalytic activity emphasized in this specification, the catalyst of the present invention has other uses such as in photovoltaics, sensors (especially gas sensors), electrochemical devices, hydrolytic catalysts. Of particular interest is the use of adsorption of visible light to catalytically split water molecules for production of hydrogen and/or oxygen gas(es).

Additionally, the catalyst can affect a large number of general chemical reactions including affect hydrophilicity/hydrophobicity of a surface exposed to the catalyst.

The products produced by the processes of the present invention are usually semiconductors. Even though described as a photocatalyst, no such activity or only incidental activity need occur for the compositions to be useful as semiconductors in a very long list of well known uses for semiconductors.

The terms catalyst and photocatalyst in the present invention are somewhat interchangeable as the catalytic activity of greatest interest is photocatalysis. Other non-photocatalytic activity may also be desirable and may be attributable to the term catalyst alone.

EXAMPLE 1

Synthesis of a Titanium Dioxide Photocatalyst Using Guanidine Nitrate 20 g of $TiCl_4$ (digested to 50% in HCl) was added to 1000 mL of water. 80 g of guanidine nitrate was added in to this solution under magnetic stirring. The resulting mixture was then heated to 100° C. Development of white color is observed within an hour. The reaction was continued at that temperature for 24 h. After the reaction was cooled to room temperature, centrifuged, and washed with water three times to remove the chlorides and any other water-soluble reactants. The product was then dried at 60° C. overnight, powdered and calcined at temperatures 350, and 450° C. for 2 h (named as Ti R350, TiR450) to obtain the final yellow colored products.

EXAMPLE 2

Alternative Synthesis of a Titanium Dioxide Photocatalyst Using Guanidine Nitrate 20 g of $TiCl_4$ (digested to 50% in HCl) was added to 1000 mL of water. 80 g of guanidine nitrate was then added to the solution and magnetically stirred for 30 minutes. Ammonium hydroxide solution was then added to bring the pH of the solution to 9. The reaction was continued at room temperature for 24 h. The ensuing precipitate was then centrifuged, washed with water three times to remove the chlorides and any other water-soluble reactants. The product was then dried at 60° C. overnight, powdered, and calcined at temperatures 350, 450 and 550° C. for 2 h (Ti350, Ti450, Ti550) to obtain the final bright yellow colored products.

EXAMPLE 3

Analysis of the Effectiveness of the Catalyst by Degradation of Methyl Orange (MO) Dye The degradation of MO was explored at varying concentrations of the catalyst (0.01-0.05 g), MO, and oxygen atmosphere. 30 mL (100 ppm concentration) of MO solution was taken in a reactor of 50 mL capacity and charged with a magnetic stir bar. 0.03 g catalyst was then added to it. The mixture was then sonicated for 2 min and inserted into a water-circulating jacket. The reaction mixture was stirred magnetically in the dark for 15 minutes to ensure the establishment of adsorption desorption equilibrium among the reactants and catalyst. After 15 minutes, two florescent light bulb of 100 watt were put on. The distance of the bulbs from the reactor was maintained at 30 cm. Aliquots were collected each ½ h.

The same reaction was repeated under the sunlight.

For reusing the catalyst, the reaction mixture was centrifuged and the collected catalyst was washed with water three times by redispersing and centrifuging. It was then washed with acetone once and then dried at 60° C. for ½ h before reusing. The catalyst Ti350 was tested and the absorbance was tested at various time intervals. The data is shown in FIG. 1 where the UV plot for the degradation of methyl orange with time using the catalyst Ti350 showed complete degradation of the dye within 3 hours.

The catalyst photocatalyzed the reaction to proceeded with the same speed with or without the presence of oxygen and no pH adjustment was necessary. This makes the catalyst unique as no added oxidant or pH adjustments are necessary for the photocatalytic degradation of the dye. While other catalysts may show a similar trend, the time required for the complete degradation of organic compounds such as methyl orange dye was much slower (in excess of 6 hours) in case of Ti550. The as-prepared catalyst did not show any activity even after 10 hours presumably because of its inability to absorb visible light as mentioned above.

The catalytic activity of the catalyst Ti350 was compared with Degussa $TiO_2$ and found that Degussa $TiO_2$ takes longer (more than 6 h) for complete degradation of MO. The effect of catalyst amount on the rate of degradation was studied. The reaction was performed using the Ti350 catalyst in different amount starting from 1 g/L to 5 g/L. It was observed the reaction becomes faster when the catalyst amount was increased from 1 g/L to 3 g/L, but remains unchanged with further increased in the amount of catalyst. The efficiency of the catalyst was then tested under sunlight. It was observed that the complete degradation of MO occurs just within 1 h. This is believed to be because of the presence of both UV and visible wavelengths in the sunlight and the strong absorption of the catalysts in the whole range of the wavelength.

EXAMPLE 4

Analysis of the Effectiveness of the Catalyst by Degradation of 2,4 Dichlorophenol (DCP)

30 mL (100 ppm concentration) of DCP solution was taken in a reactor of 50 mL capacity and charged with a magnetic stir bar. 0.03 g catalyst was then added to it. The mixture was then sonicated for 2 min and inserted into a water-circulating jacket. The reaction mixture was stirred magnetically in the dark for 30 minutes to ensure the establishment of adsorption desorption equilibrium among the reactants and catalyst. After 30 minutes, two florescent light bulb of 100 watt were put on. The distance of the bulbs from the reactor was maintained at 30 cm. Aliquots were collected each 1 h and the degradation was monitored by using the UV peak at 289.7 nm.

Figure 2:
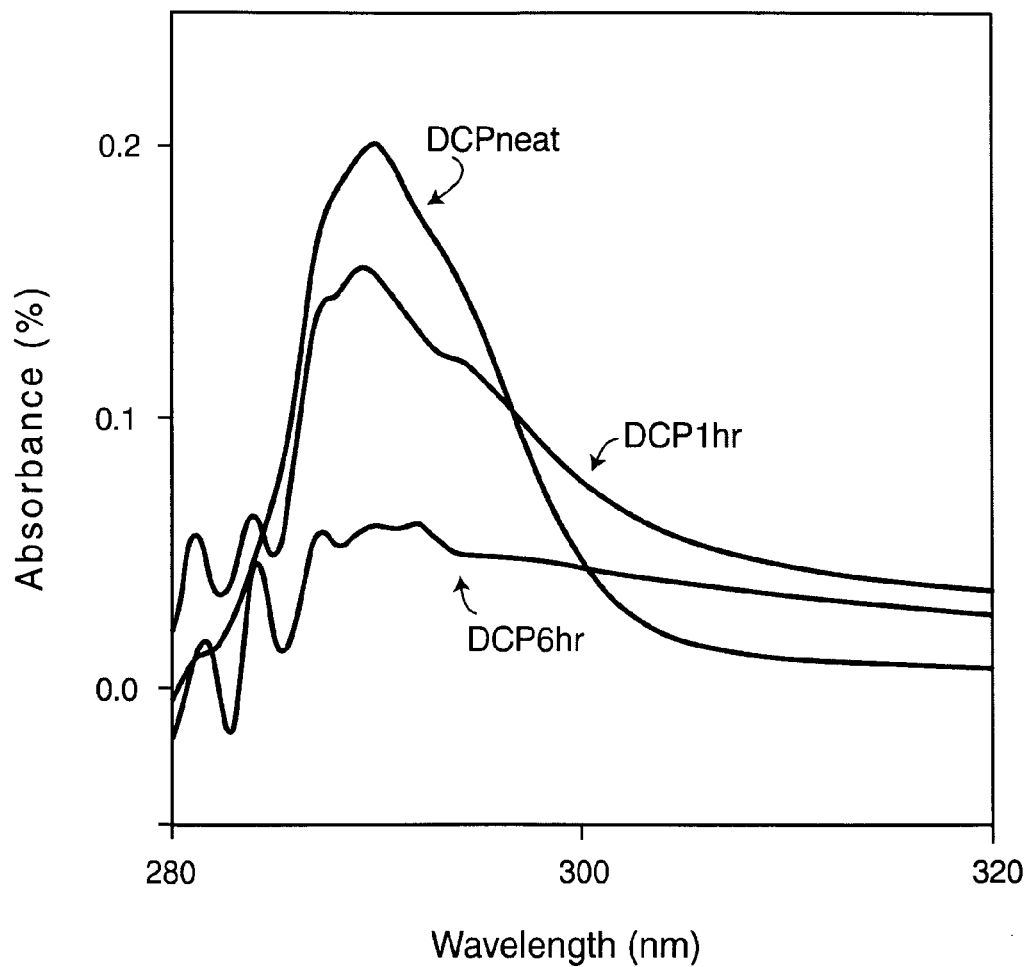
FIG. 2 is a graph showing degradation of dichlorophenol with time.

After standardizing the reaction conditions related to the amount of catalyst, reaction time etc., the catalyst system was tested for degradation of the water pollutant DCP. The catalyst was active for the degradation of DCP under the same household used lightbulbs as well as sunlight as in the previous Example. The complete degradation of DCP was achieved in 6 h. The degradation was monitored by the UV peak at 289.77 nm. The intensity of the peak decreases with time and ceases to exists after 6 h confirming the absence of any DCP in the solution within the detection limit of the instrument. FIG. 2 is the corresponding UV plot for the degradation of DCP with time.

EXAMPLE 5

Analysis of the Catalyst Formed

The phase of the as-synthesized $TiO_2$ nanoparticles was determined by X-ray diffraction in an MMS X-ray diffractometer with a Cu Kα source in the 2θ range 10 to 80. The data were collected with a step of 1 deg/min. A few drops of the as-synthesized nanoparticles in isopropyl alcohol were added to a quartz plate and dried at room temperature before recording the X-ray pattern. TEM micrographs were recorded on a Phillips CM 20 TEM microscope at an operating voltage of 200 kV. A drop of the as-synthesized nanoparticles in ethanol was loaded on a carbon coated copper grid and then allowed to dry at room temperature before recording the micrographs. The UV DRS spectra were recorded on a Shimadzu UV-250IPC instrument in the range 200 to 800 nm. The UV spectra for following the decomposition of MO and DCP were recorded on a Hewlett Packard 845X UV-Visible instrument. The Surface area measurement was carried out in a Micromeritics single point BET instrument.

The materials synthesized are confirmed to be $TiO_2$ by X-ray diffraction. The sample Ti350 is purely anatase while the other samples contain varying percentages of rutile phase depending on the calcination temperature. The sample Ti350 has crystallite size of 6.77 nm while the sample Ti550 has a crystallite size of 17.8 nm. The crystallite size increases with the increase of calcination temperature.

Particle sizes are found to be in the range 6 nm to 20 nm with a very narrow size distribution from the TEM micrographs. Little agglomerations are observed in the sample Ti350, but severe agglomerations could be observed in case of the sample TiR350. This may explain its decreased catalytic activity compared to Ti350.

Figure 3:
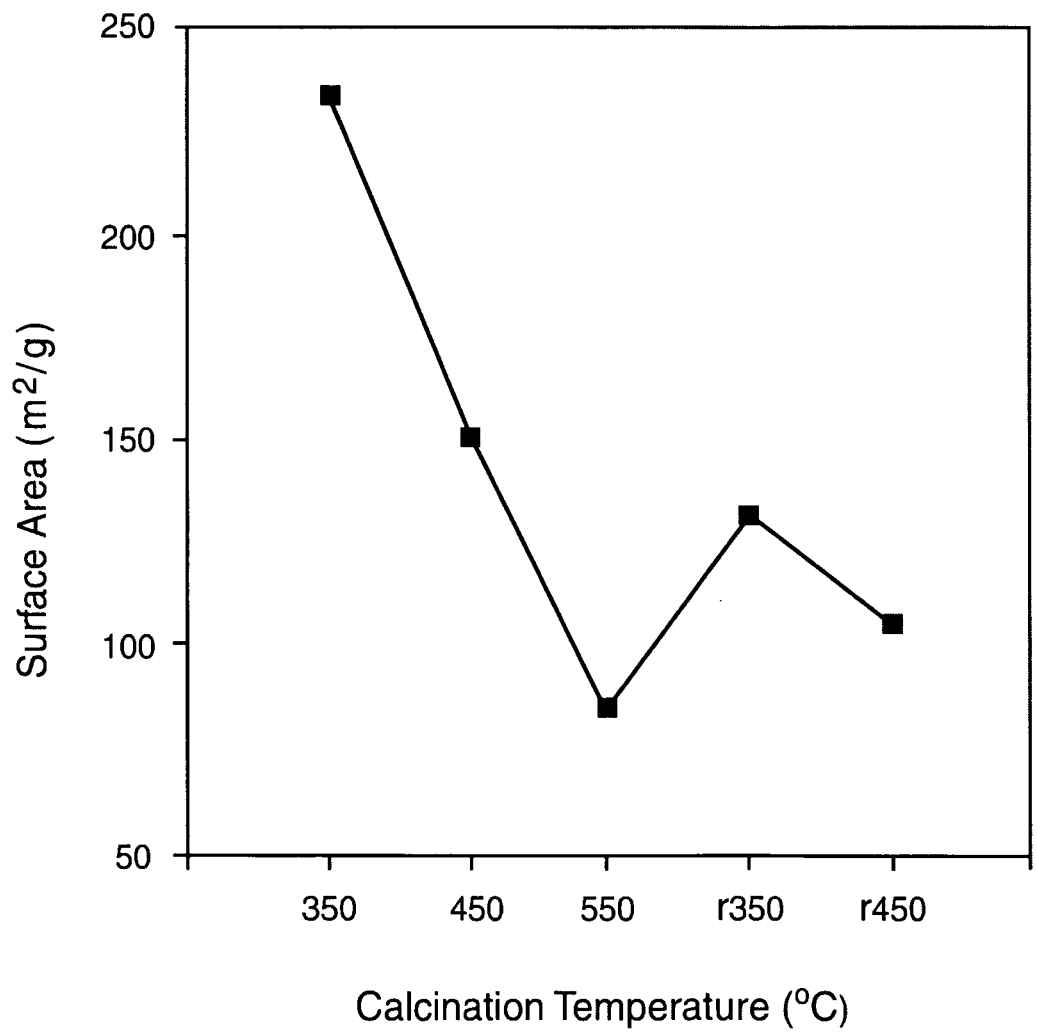
FIG. 3 is a graph showing BET surface area of the synthesized samples corresponding to the calcination temperatures.

BET surface area measurements show the sample Ti350 has the highest surface area of 233 $m^2/g$. There is a regular trend of decrease in surface area with increasing calcination temperature that could be correlated to the increase in crystallite as well as particle sizes. The surface area found for Ti450 was 150 $m^2/g$ while for the sample Ti550 it is 85 $m^2/g$. The surface areas for the samples TiR350 and TiR450 are found to be 133 $m^2/g$ and 105 $m^2/g$ respectively. The decrease in surface area could be related to the agglomerations. FIG. 3 shows the plot of the surface area vs. calcination temperature for the synthesized samples. The surface area of the samples directly correlates to the photo catalytic activity of the samples.

The visible light activity of the synthesized samples was realized by their absorption edges depicted by the UVDRS spectra. The absorption vs. wavelength plots for the synthesized samples clearly shows the extension of the absorption band to the visible region. The sample Ti350 has two sharp absorption bands at 433 nm and 562 nm respectively, clearly depicting its high photo catalytic efficiency in the visible light. Sample Ti450 has comparable efficiency with Ti350, which is evident from its absorption wavelengths in its UVDRS plot. Sample Ti550 has its sharp absorption mainly in the UV region and only a slight absorption in the visible region could be discerned. This lower absorption in the visible region leads to its declined photocatalytic efficiency under visible light. The as-prepared sample does not have absorption in the visible region that explains its non-reactivity under visible light. Sample TiR350 does not have two absorption bands. The absorption wavelength for this sample is around 450 nm that explains its lower catalytic activity under visible light. The shifts in the absorption bands could be explained on the basis of new surface states or polarizations introduced by the anionic dopants in to $TiO_2$.

The catalyst was found to be almost equally active at five repeated cycles after which the time required for the complete degradation increases to 6 h. The reason for the drop is unclear but may be because of the absorption of foreign moieties on the surface that blocks the catalytic sites. The catalyst is then regenerated by washing with water several times followed by one washing with acetone and then drying at 200° C. for 6 h.

EXAMPLE 6

Synthesis of a Titanium Dioxide Photocatalyst Using Melamine

N-doped $TiO_2$ nano-powders were prepared by a simple sol-gel method: i) 20 g of $TiCl_4$ (digested to 50% in HCl) was dispersed in 1000 ml of distilled water. Then 80 g of melamine was added to the solution and magnetically stirred for 30 min. The amount of dopant was calculated based on the assumption that in order to assure an increased photocatalytic activity, the content of nitrogen in the catalyst after hydrolysis should not be less than 0.5 wt % of the catalyst dry mass. Therefore, the ratio between the molar concentration of $Ti^{4+}$ and melamine was maintained 1:4.

Ammonium hydroxide ($NH_4OH$, 33 wt %) solution was added to bring the pH of the solution to 9. The reaction was then stirred for 24 h at room temperature and atmospheric pressure. The final product was dried at 60° C. overnight in air, powdered, calcined at 450° C. for 2 h and characterized by means of thermogravimetric analysis (TGA), X-ray diffraction (XRD), diffuse reflectance spectroscopy (DRS) and scanning electron microscopy (SEM-EDS). Yellow color of calcined N-doped $TiO_2$ suggested its ability to absorb light in the visible region.

The UV DRS spectra were recorded on a Shimadzu UV-250IPC instrument in the range 200 to 800 nm. Crystal structure patterns of N-doped $TiO_2$ powder samples were examined by X'Pert Pro MPD X-ray diffractometer with a Cu Kα source and diffraction angle range of 2θ=10 to 70°. The data was collected at a step of 1 degree/minute and a typical angle of 0.5°. The average crystallite size (d) was calculated as a function of the peak width (d=Kλ/β cos θ) according to the Sherrer's equation, where λ is the wavelength of X-rays (0.154 nm Cu Kα), β is the full width at half maximum (FWHM) in radian and θ is the Bragg angle in degrees. The thermogravimetric analysis (TGA) was performed using TGA Q5000 (TA Instruments) analyzer with a heating rate of 10 degrees/min in an air flow employing a ramp method (temperature increase from 100 to 1200° C.). The morphology and elemental composition analysis were performed by scanning electron microscopy (SEM, FEI XL30 ESEM) equipped with EDS (energy dispersive X-ray spectroscopy) operating at 15-30 kV on gold-sputtered samples. TEM micrographs were recorded on a Phillips CM 20 TEM microscope at an operating voltage of 200 kV.

EXAMPLE 7

Properties of the Photocatalyst Formed by Example 6

Figure 4A:
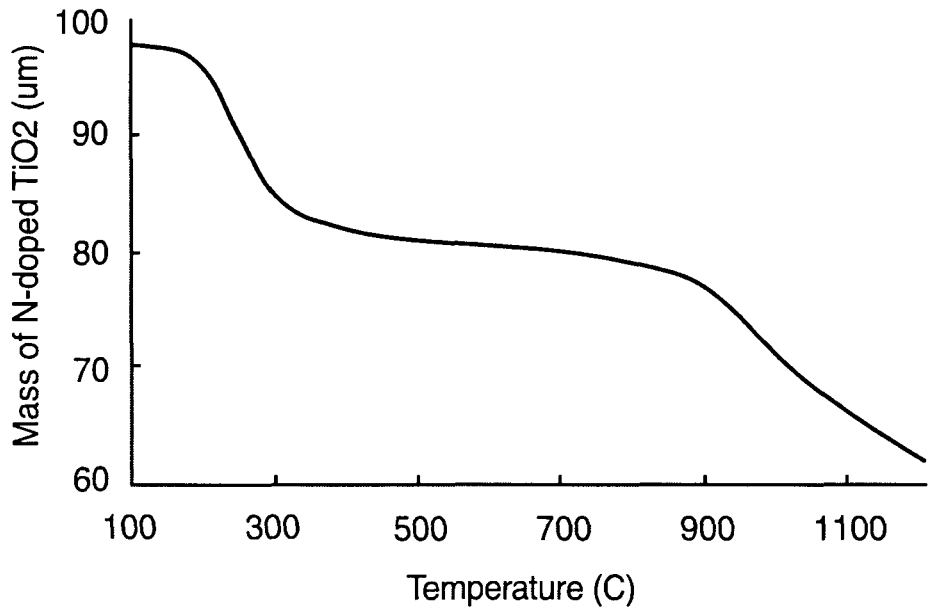
FIG. 4a is graph showing the thermogravimetric spectra.

FIG. 4a presents a thermal decomposition profile of N-doped $TiO_2$ in air. There are three distinct regions at 100-150, 250-300 and 700-1100° C. The weight loss in the first region may be attributed to the adsorbed water; the second is due to the decomposition of free and non-complexed melamine, whereas last region may be assigned to the degradation of residuals, which are formed during the oxidation of melamine.

Figure 4B:
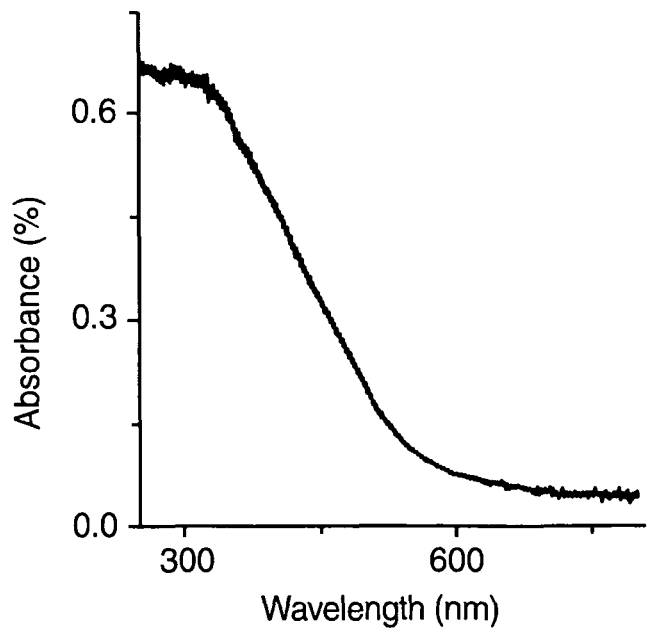
FIG. 4b is a graph showing UV-vis Diffuse reflectance spectra for N-doped TiO2 nanocatalyst calcined at 450° C.

Diffuse reflectance UV-vis spectra is presented in FIG. 4b. It shows the adsorption of N-doped $TiO_2$ in the visible light region. The band gap energy was 2.2 eV in the nano N-doped $TiO_2$, which was estimated for the absorption edge[17] (E (eV) =1240/λ (nm)), where the adsorption threshold was 568 nm. The first edge (~400 nm) may be attributed to the band structure of original titania, whereas the edge at 568 nm is assigned to the newly formed N 2p band (FIG. 1b). The band gap narrowing may be attributed to the doping of interstitial N species, i.e. the narrowing of isolated N 2p band formed above the O 2p valence band.

SEM image of N-doped $TiO_2$ nanocatalyst calcined at 450° C. shows that N-doped $TiO_2$ powder is agglomerated at some degree after calcination with some larger particles that remain intact by the temperature. The EDS data of N-doped $TiO_2$ shows Nano catalyst with a peak around 0.2-0.3 keV, which is attributed to $TiO_2$ surface and an intense peak at about 4.5 keV, which is assigned to $TiO_2$ in the bulk form. TEM images of N-doped $TiO_2$ clearly show no porous structure was formed during calcination at 450° C. and nearly cubical particles prevailed. Moreover, the particle size in N-doped $TiO_2$ nanocatalyst was less than 20 nm, which is in a good agreement with that obtained from XRD patterns.

X-ray diffraction pattern of N-doped $TiO_2$ photocatalyst clearly shows the as-prepared photocatalyst exhibited an XRD pattern that can be attributed to anatase with strong peaks at 25°, 38° and 48°. The average crystallite size of N-doped $TiO_2$ calculated from Sherrer's equation was 17.3 nm.

EXAMPLE 8

Analysis of the Effectiveness of the Catalyst by Degradation of Methylene Blue (MB)

Photobleaching of methylene blue (MB) as the model pollutant was quantified by measuring its degradation rates under visible light in the presence of synthesized N-doped $TiO_2$ photocatalyst. 3 g $L^{-1}$ of as-prepared N-doped $TiO_2$ was dispersed in 20 ml of fresh MB solution (100 ppm). Before irradiation, the reaction suspension was magnetically stirred in the dark for 30 min to obtain an equilibrium of MB onto the N-doped $TiO_2$ surface. Moreover, the un-adsorbed MB concentration (80.3 ppm) was taken as the initial concentration to evaluate the efficiency of photobleaching. A medium pressure metal halogen desk lamp (300 W) was used as a visible light source. To cut the infrared irradiation, the glass reactor was inserted into the water circulating jacket and continuously bubbled with $O_2$. The MB photobleaching was monitored by collecting time-sequenced (every 60 min) aliquots, which were subsequently filtered through 0.45 μm PTFE syringe filter to remove $TiO_2$ particles. The absorption spectrum was recorded using Hewlett Packard 854 X UV-Visible instrument at maximum peak of 664 nm from which the photocatalytic activity was evaluated. Triple photocatalytic experiments were performed under the identical reaction conditions to determine reproducibility.

Figure 5:
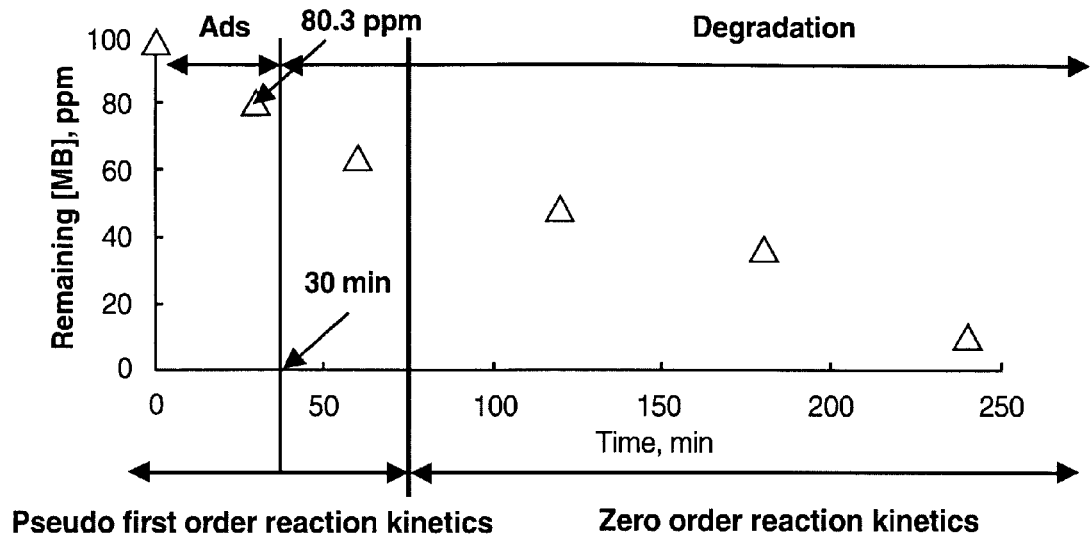
FIG. 5 is a graph of Visible light induced photobleaching of methylene blue over N-doped TiO2 nanocatalyst.
Figure 5A:
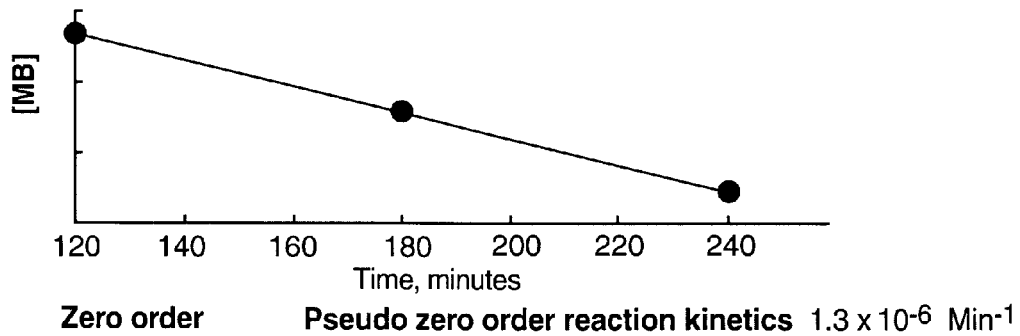
Figure 5B:
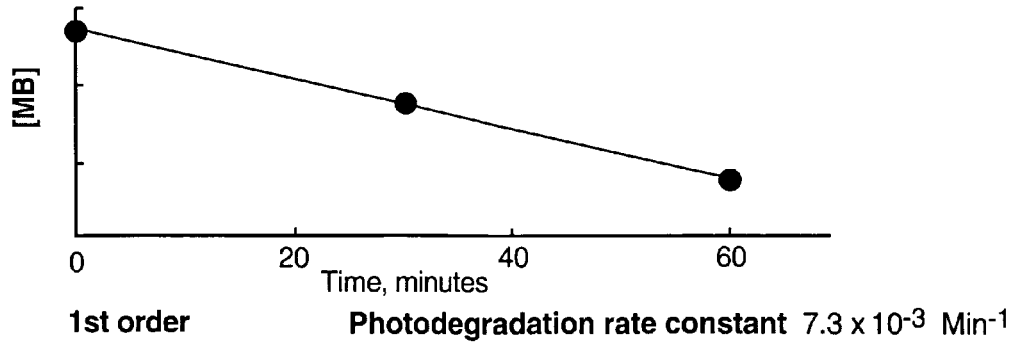

The visible light induced photobleaching of MB over N-doped sample as a function of MB concentration versus irradiation time is shown in FIG. 5. It can be seen that a complete decomposition of MB was achieved within 240 min of the irradiation. The degradation of MB followed a mixed order reaction kinetics with an 'induction' (pseudo first order reaction kinetics, photo degradation rate constant of $7.3 \times 10^{-3}$ min$^{-1}$) and a subsequent 'acceleration' (pseudo zero order reaction kinetics, $1.3 \times 10^{-6}$ M min$^{-1}$) period. During an induction period, the reaction rate depended on the concentration of MB in the solution, whereas during the acceleration period, it was assumed that no build up of reaction intermediates was present and the surface of the catalyst became saturated with the reactant. Therefore, the reaction proceeded independent of the MB concentration.

High photocatalytic activity of the N-doped TiO$_2$ samples were assigned to the activity of highly crystalline anatase. Moreover, as oxygen was continuously supplied to the reaction system, electrons were trapped in the conduction band to form $.O_2^-$ which could subsequently generate active .OOH radicals[5] that contributed to the increased photobleaching of MB.

EXAMPLE 9

Synthesis of a Titanium Dioxide Photocatalyst Using Guanidine Nitrate and Silver Nitrate Photoactive TiO$_2$ powders were prepared under the room temperature by a simple sol-gel procedure: i) Ag/TiO$_{2-x}$N$_x$ was prepared by dispersing of 20 g of Ti$^{4+}$ salt (digested to 50% in HCl) to 1000 mL of water. Then 20 g of guanidine nitrate and 5 mol % of AgNO$_3$ was added to the solution and magnetically stirred for 30 minutes. Ammonium hydroxide (NH$_4$OH, 33 wt %) solution was then added to bring the pH of the solution to 9. The reaction was carried out at room temperature for 24 h. The product was dried at 60° C. overnight, powdered, calcined at 450° C. for 2 h and characterized by means of X-ray diffraction (XRD), TEM, and SEM-EDS. Ag/TiO$_{2-x}$N$_x$ were yellow or light yellow suggesting their ability to absorb light in the visible region.

EXAMPLE 10

Properties of the Photocalyst formed by Example 9

The XRD patterns were determined by X-ray diffraction in a X'Pert Pro MPD X-ray diffractometer with a Cu Kα source with the diffraction angle range of 2θ=10 to 70°. The data was collected at a step of 1 deg/min and a typical angle of 0.5°. SEM observations were performed using a FEI XL30 ESEM, operating at 15-20 kV on gold-sputtered samples. TEM micrographs were recorded on a FEI CM20 TEM microscope at an operating voltage of 200 kV.

SEM clearly shows the distribution of the dopants on or inside the TiO$_2$ lattice. EDS-pattern of Ag/TiO$_{2-x}$N$_x$ particles are also be seen. There are eight X-ray peaks associated with O Kα, Mg Kα, Al Kα, Au Kα, Cl Kα, Pd Kα, Ag Kα and Ti Kα, however, lines of Mg Kα, Al Kα, Au Kα, Cl Kα, Pd Kα are either constituents of the TEM grid used for the analysis, precursors of the synthesis or impurities. Therefore, results indicate that O, Ag and Ti correspond to the nanoparticles prepared by the aforementioned protocol.

It was evident that silver and TiO$_2$ particles were nearly spherical. The density of silver particles is higher than that of TiO$_2$, therefore the TEM image of the silver particle is much darker in comparison to TiO$_2$.

The average crystallite size can be determined from the semi-empirical Sherrer's equation (d=Kλ/β cos θ) taking into account the half-width of the major diffraction peaks, where λ is the wavelength of X-rays (0.154 nm), β is the full width at half maximum in radian and θ is the Bragg angle in degrees. The mean crystallite size derived from Sherrer's equation was 29.3 nm. The formed metallic silver particles had strong peaks at 38° (111), 44.6° (200) and 65.7° (220) indicating that Ag was efficiently attached to TiO$_2$. Ag/TiO$_{2-x}$N$_x$ exhibited strong TiO$_2$ peaks at 25°, 37.8° and 48°. The rutile phase, which was not detected in Degusa P25 sample, at 28.3° may be attributed to the deposited Ag particles.

EXAMPLE 11

Analysis of the Effectiveness of the Catalyst by Degradation of Methyl Orange (MO)

The photocatalytic activity of Ag/TiO$_{2-x}$N$_x$ was evaluated by degradation of methyl orange (MO). For the photocatalytic experiments, unless specified otherwise, 20 mL (100 ppm) of MO aqueous solution was placed in a 25 mL glass reactor equipped with a magnetic stirrer. 3 g/L of the freshly prepared catalyst was dispersed into the solution. The mixture was inserted into a water circulating jacket to cut the infrared radiation and continuously fluxed with O$_2$. The reaction mixture was stirred magnetically in the dark for 30 minutes to ensure adsorption/desorption equilibrium between the contaminant and the catalyst. The photoreactor was irradiated using a 300 W medium pressure Hg lamp. MO degradation was monitored by collecting aliquots at regular time (30 min and 1 hour, unless indicated otherwise) intervals. The aliquots were centrifuged and absorption spectra were recorded using Hewlett Packard 845X UV-Visible instrument at maximum peak of 464 nm.

The visible light induced photocatalytic mechanism of Ag/TiO$_{2-x}$N$_x$ photocatalytic reaction pathway of MO is proposed as following:

1) Silver ions undergo transformation on the TiO$_2$ surface at 450° C. calcination temperature:

$$AgNO_3 \rightarrow Ag_2O \rightarrow Ag \qquad (1)$$

2) The presence of silver particles and nitrogen helps to efficiently split the electron hole pairs by attracting the conduction band photoelectrons. Moreover, the valence band photogenerated holes are able to react with OH$^-$ adsorbed onto the TiO$_2$ to create hydroxyl radicals (.OH):

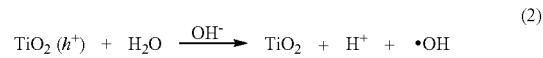

$$TiO_2(h^+) + H_2O \xrightarrow{OH^-} TiO_2 + H^+ + \bullet OH \qquad (2)$$

3) Furthermore, the conduction band electrons can react with electron acceptors (e.g. O$_2$) producing oxygen radicals (O$_2^-$):

$$TiO_2(e^-) + O_2 \rightarrow TiO_2 + .O_2^- \qquad (3)$$

4) In addition, the electron migrates to the surface of the TiO$_2$ catalyst, where it participates in the reduction of MO (anionic basic form MO$^-$) in the presence of powerful oxidizing agents:

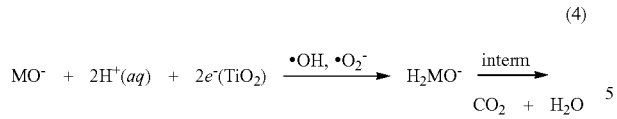
(4)

Figure 6:
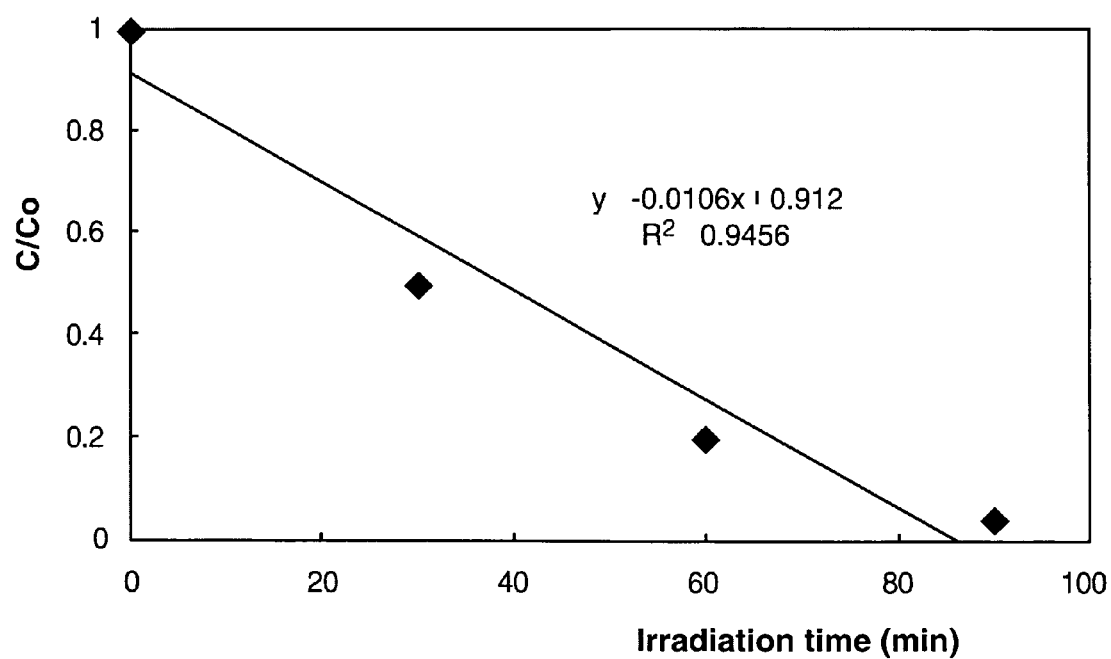
FIG. 6 is a graph showing the ratio between the concentration of methyl orange (C), at a certain time (t), and the initial concentration ($C_o$) in the presence of $Ag/TiO_{2-x}N_x$ catalyst and visible light.

FIG. 6 shows a ratio between the concentration of methyl orange (C) at a certain time, t, and the initial concentration ($C_o$) in the presence of $Ag/TiO_{2-x}N_x$ catalyst and visible light. The reaction followed the pseudo zero order with the reaction rate of $5.3 \times 10^{-5}$ M s$^{-1}$. Initial tests showed that adsorption onto the $Ag/TiO_{2-x}N_x$ surface was negligible and comprised only 20%. Catalyst calcined at 450° C. and doped with 5 mol % Ag showed excellent photocatalytic activity and MO was completely degraded in 90 min. Increased photocatalytic activity may also be also attributed to the formation of active inorganic radical anions, such as $NO_3^-$ from guanidine nitrate:

(5)

Moreover, $Ag/TiO_{2-x}N_x$ exhibited an outstanding stability and reusability, without the significant loss in the catalytic activity (reaction rate constants were 5-15% lower than that of the original catalyst) after 5 experimental rounds. However, after the simple regeneration procedure of Example 5, the catalyst showed similar photocatalytic activity (reaction rate constants in average 3-5% lower) in comparison to the original $Ag/TiO_{2-x}N_x$.

The addition of silver to the doping agent resulted in enhanced photocatalytic activity as compared to the guanidine nitrate alone.

EXAMPLE 12

Synthesis of a Titanium Dioxide Photocatalyst Using Silver Nitrate and Garlic

The typical sol-gel synthesis of Ag, S co-doped $TiO_2$ nanoparticles is as follows: Titanium tetraisopropoxide (TTIP), glacial acetic acid and water were used in the molar ratio of 1:10:300. TTIP was mixed with glacial acetic acid in the ice bath and 5 mol % of $AgNO_3$ along with freshly crushed garlic dispersed in water was added to the mixture under vigorous stirring. To prepare a sulfur dopant, a few garlic cloves were crushed using a regular blender. Bigger garlic chunks were removed and the resulting garlic slurry was further dispersed in water and added to the TTIP, glacial acetic acid and $AgNO_3$ mixture. When this mixture turned to be a sol, it was stirred for 8 h and aged for 48 h in the room temperature to form a gel. The ageing results in the substantial structural reorganization of the gel network, which may lead to the change in structure and properties of the materials prepared. The gel was then dried in an oven at 70° C. for 12 hours and crushed well. The resulting powder was then calcined in air at 450° C. and 700° C. for 2 hours.

EXAMPLE 13

Properties of the Photocatalyst Formed by Example 12

The X-ray diffraction (XRD) patterns of Ag, S-codoped $TiO_2$ nanocatalysts were recorded on a X'Pert Pro MPD X-ray diffractometer in the range of $2\theta=10-80°$ with a count time of 20 s at each point using Cu $K\alpha$ radiation as the X-ray source. The accelerating voltage and applied current were 45 kV and 40 mA, respectively. The crystallite size of samples was calculated by using Scherrer equation:

$$Dp = \frac{0.9\lambda}{\beta \cos\theta} \quad (1)$$

where Dp is the crystallite size (nm), $\lambda$ is X-ray wavelength (0.154056 nm), $\theta$ is the Bragg angle and $\beta$ is full width at half maximum (FWHM). FWHM of each diffraction line was determined from the profile measured with a scanning rate of $\frac{1}{2}°$ ($2\theta$) min$^{-1}$, which was calibrated by standard silicon powder for instrumental broadening. Lattice strain $\epsilon$ of anatase phase was determined accordingly:

$$\varepsilon = \frac{\beta}{4\tan\theta} \quad (2)$$

The phases were identified with the aid of Joint Committee on Powder Diffraction Standards (JCPDS). Transmission electron microscopic (TEM) images were recorded using FEI CM20 TEM operating at an accelerated voltage of 160 keV. The samples were dispersed in ethanol by an ultrasonic irradiation for 20 min and a drop of the suspension was placed onto a lacey carbon coated copper grid. Moreover, the grid was dried in air prior to imaging. The morphology of samples was observed using scanning electron microscopy (FEI XL 30 ESEM), operating at 15-20 kV on gold-sputtered samples.

XRD Analysis

X-ray diffraction patterns of nano Ag, S-codoped $TiO_2$ and commercial Degussa P25 calcined at 450° C. and 700° C. were measured. The mean crystallite sizes (Dp) calculated using Sherrer equation and lattice strains ($\beta \cos \theta$) of as-prepared nanophotocatalysts are presented in Table 1. At both calcination temperatures of 450° C. and 700° C., the principal crystalline phase was anatase (tetragonal, a=b=3.78 Å; c=9.50 Å) with some minor traces of brookite (rhombohedral, a=5.43 Å, b=9.16 Å, c=5.13 Å) and rutile (tetragonal, a=b=4.58 Å, c=2.95 Å)[18] phase which started to appear at 700° C. (FIG. 2). The diffraction lines were well-defined and sharp with an increase in calcination temperature.

Moreover, the shape, the intensity and the width of diffractive peaks of the crystal planes of Degussa P25, S-doped $TiO_2$ and Ag, S-codoped $TiO_2$ calcined at 700° C. and were quite similar. However, the width of (101) plane in Ag, S-codoped $TiO_2$ sample was much broader and less intense in comparison to the rest of the samples indicating a sharp decrease in the crystallite size.

Figure 7:
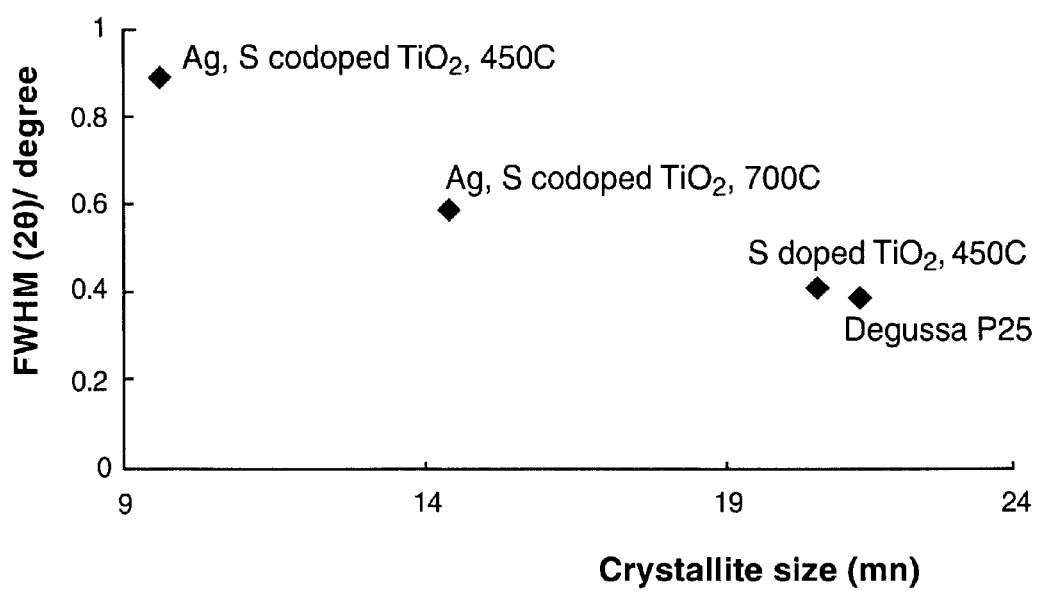
FIG. 7 is a graph that shows the relationship between FWHM and the crystallite size of as-prepared doped and co-doped nano $TiO_2$ photocatalysts.

FIG. 7 (FWHM) shows the relationship between the FWHM and the crystallite size of nanocatalysts calcined at 450° C. and 700° C. Thus, an increase in the intensity and sharpening of the diffraction peak of anatase phase in Ag, S-codoped sample calcined at 700° C. may have also been caused by the elevated calcination temperature, which forced condensation of free OH groups on the surface of $TiO_2$ nanoparticle.[4] Such condensation of OH groups causes the formation of an oxygen vacancy which can be doped with an anion/cation, for instance ($S^{2-}$). It should be noted that the diffraction peak of Ag, S-codoped $TiO_2$ calcined at 700° C. shifted to the wider angle (25.21°) in comparison to the Degussa P25 sample (25.16°) and S, Ag co-doped or S-doped nano $TiO_{2)}$(25.07°). This suggest that some of the $Ti^{4+}$ ions may be substituted by $Ag^+$ ions at elevated temperature, which may have caused the distortion of the lattice which subsequently led to the diffraction peak shift to the wider angle. Moreover, the crystal lattice may also be distorted by incorporating of cationic sulfur species into TiO$_2$ either interstitially or at the lattice sites.

According to Periyat and co-workers, kinetically more stable anatase phase starts transforming to rutile after growing to a crystallite size of more than 14 nm whereas below 14 nm, the anatase phase is the most stable one. Thus, S-doped (Dp=20.5 nm) and Ag, S co-doped TiO$_2$ (Dp=14.4 nm) nanocatalysts, regardless the calcination temperature, are more prone to the transformation to the rutile phase. The absence of the featured rutile phase at 450° C. and 700° C. revealed that the as-prepared nanocatalysts were stabilized by dopants introduced onto the TiO$_2$ surface. Furthermore, these findings also indicate that the dopants play a significant role in the crystallite growth and the stability during the sol-gel process at the selected temperature range.

In Degussa P25 sample, a trace of rutile phase at 27.4° (110) was observed and was attributed to its natural occurrance due to the particular synthesis of the commercial product (75% anatase:25% rutile phase). Anatase phase showed a strong representative peaks at 25°, 37.8° and 48° due to the 101, 004 and 200 planes (JCPDS 21-1272), respectively. It is important to indicate that crystallite size increased and lattice strain decreased with an increase in the calcination temperature from 450° C. to 700° C. and with the doping of TiO$_2$ with Ag$^+$ ions (Table 1).

The relatively small Dp may be attributed to the synthesis conditions: i) a large amount of water was used to increase the nucleophilic attack of water on TTIP in order to suppress the TTIP species to yield nanocrystals, ii) acetate anion that is adsorbed on the TiO$_2$ surface may restrain the nanoparticles from further growth and iii) dopants that may suppress the growth of the nanocrystals.

Metallic silver particles exhibited strong peaks at 38° (111), 44.6° (200) and 65.7° (220) indicating the Ag attachment to the TiO$_2$ surface. In addition, no sulfur phase and only a trace amount of TiS$_2$ was observed in the S-doped TiO$_2$ sample. Thus, sulfur ions were uniformly dispersed among the anatase crystallite.

SEM and TEM Analysis

Selected SEM images of Ag, S co-doped TiO$_2$ calcined at 450° C. and 700° C. were taken. The as-prepared nanocatalysts consisted of nearly spherical particles and aggregation took place during the nanoparticle formation process.

The shape of the particles remained unchanged regardless the calcination temperature applied. Catalyst particles calcined at 450° C. were aggregated into clusters in the range of several hundred nanometers, however the increase in calcination temperature improved the dispersion and reduced the agglomerate size to tens of nanometers of co-doped TiO$_2$. TEM images of modified TiO$_2$ demonstrated that the particle sizes of samples calcined at 450° C. and 700° C. was ranging from 10 to 20 nm, which was consistent with the XRD data.

EXAMPLE 14

Analysis of the Effectiveness of the Catalyst of Examples 12 and 13 by Degradation of Methyl Orange (MO)

Figure 8:
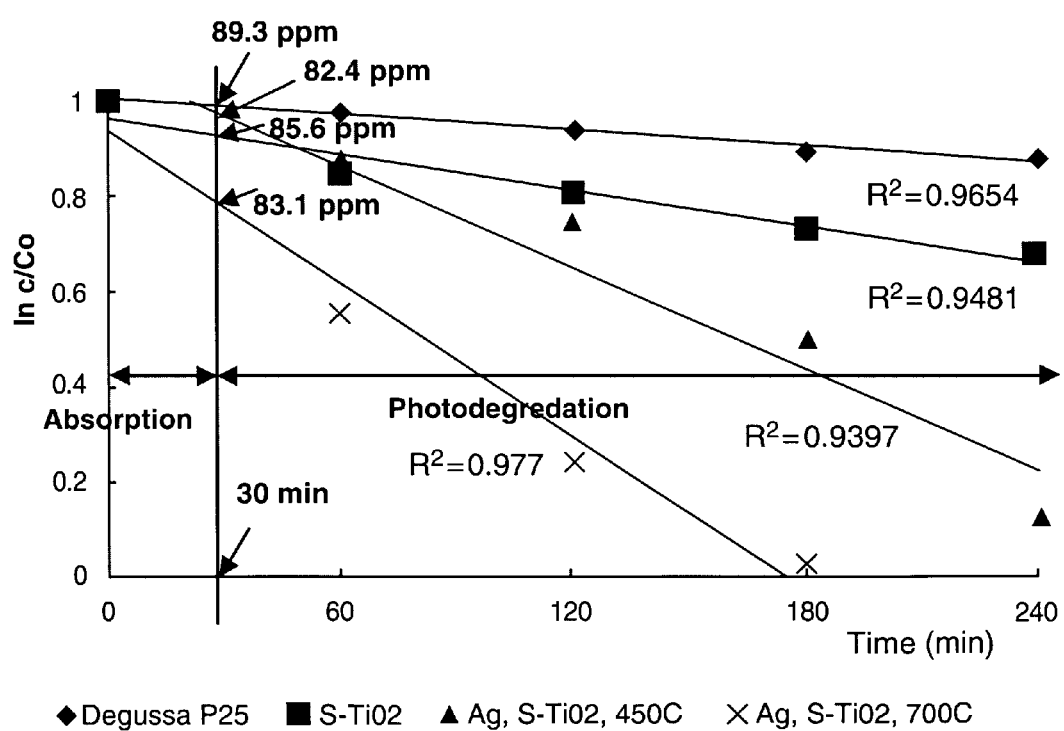
FIG. 8 is a plot of relative concentrations of MO in logarithmic scale ($\ln(C/C_o)$) against the irradiation time (t) for Ag, S-codoped $TiO_2$, S-doped $TiO_2$ and commercial Degussa P25 calcined at 450° C. and 700° C.

The typical liquid-phase photocatalytic degradation of methyl orange (MO) was performed at room temperature (25±1° C.) in 20 mL quartz photochemical reactor containing 3 g L$^{-1}$ of catalyst and 100 ppm of MO aqueous solution (FIG. 8).

The photocatalytic reactor was equipped with a magnetic stirrer and accommodated in the water cooler for the adequate temperature control. All the UV irradiation with the wavelength less than 420 nm was removed by a cutoff glass/water filter. The photocatalytic reactor and the light source were positioned inside the black metal box to prevent the light leakage. To determine the adsorption equilibrium, suspension was aerated and irradiated in the dark for 3 h with aliquots taken every 15 min and subsequently analyzed for the residual MO concentration. After 30 min of the reaction with various catalysts, MO concentration remained constant, therefore the respective concentration was adopted as the initial (from 82.4 to 89.3 ppm) and the photocatalytic treatment was initiated. The reaction system was irradiated with 300 W metal halogen desk lamp located approx. 15 cm away from the solution. Concentration of MO in the reaction solution was measured as the function of irradiation time of 4 h unless indicated otherwise. At regular intervals (every 60 min), 3 mL of aliquots was withdrawn from the solution, passed through a 0.45 μm syringe filter and analyzed by a UV spectrophotometer (Hewlett Packard 845X) at the characteristic wavelength (464 nm) to determine the MO degradation efficiency using earlier established calibration curve. In addition, preliminary tests were carried out without the addition of the catalyst in the presence of the visible light irradiation. Less than 1% of MO degraded after 4 h of the reaction, thus could be ignored in comparison to the results obtained in the presence of both, the nanophotocatalyst and the visible light irradiation. The reproducibility of the results was assured by experiments performed in triplicates and was found to be within 5-7%. The rate of MO degradation was assumed to obey pseudo-first order reaction kinetics and, therefore, the photo-degradation rate constant, k (min$^{-1}$) was obtained according to the power rate law:

$$-\frac{d[A]}{dt} = k[A] \tag{3}$$

This equation may be further integrated to:

$$-\ln\left(\frac{A}{A_o}\right) = kt \tag{4}$$

$$[A] = [A]_o e^{-kt} \tag{5}$$

where $A_o$ is the initial MO concentration (ppm), A is the concentration after time (t, min) and k is the pseudo-first order reaction rate constant (min$^{-1}$).

Leaching of Silver Ions from the Catalyst

The leaching of silver ions from the as-prepared catalyst was qualitatively tested by adding 5 ml of 1 M NaCl solution to the MO aqueous solution either after irradiation for 30 min or in the absence of the visible light, with and without the presence of 3 g L$^{-1}$ catalyst.

Photocatalytic Activity

The visible light induced oxidation of MO over doped nano TiO$_2$ obeyed the Langmuir-Hinshelwood first order reaction kinetics (Eq. 1-4). According to Beer-Lambert law:

$$A = \epsilon \times L \times [MO^-] \tag{11}$$

where A is the maximum absorbance of [MO$^-$] at the wavelength 464 nm, ε is the molar absorbtivity (L mol$^{-1}$ cm$^{-1}$), L is the path length of the sample (cm) and [MO$^-$] is the concentration of the compound in solution (mol L$^{-1}$). Molar absorptivities for Degussa P25, S doped TiO$_2$, Ag, S co-doped TiO$_2$ calcined at 450° C. and 700° C. were 0.38, 0.43, 0.45, 0.45 $M^{-1}$ $cm^{-1}$, respectively and were expected to be a linear decreasing function of time. The Beer Law states that the absorption is proportional to the concentration of absorbing species in the aqueous solution; therefore the maximum absorbance was directly proportional to the concentration of [$MO^{-1}$] in the reaction solution (Eq 11).

The photocatalytic activities of as-prepared nanocatalysts were evaluated by the reaction rate constants (Table 1). It is known that azodyes can absorb visible light themselves.[4] Therefore, to evaluate the hypothesis that the degradation of MO can be attributed to the self-sensitization mechanism or the addition of the nanocatalyst, several experiments were performed without $TiO_2$ and only in the presence of the visible light irradiation. These experiments showed that the significant degradation (only 5-8%) of MO did not occur in the absence of the nanocatalyst and only a negligible amount of MO (8-12%) was destroyed in the absence of visible light due to the adsorption of azodye onto the surface of the doped and co-doped $TiO_2$. The decrease in MO concentration was attributed to the chemical reaction rather than adsorption.[3] According to the kinetic model applied, the reaction rate constants were $1.6\times10^{-3}$, $8.5\times10^{-3}$ and $19.4\times10^{-3}$ $min^{-1}$ for S doped $TiO_2$, Ag, S co-doped $TiO_2$ calcined at 450° C. and 700° C., respectively, while $5.3\times10^{-4}$ $min^{-1}$ was observed for Degussa P25 (Table 1). It is obvious that the visible-light activity was significantly enhanced by the addition of dopants, especially for Ag, S-co-doped $TiO_2$ calcined at 700° C. (FIG. 8).

Degussa P25, which was selected as a reference, showed some activity towards the degradation of MO, which may be attributed to the photosensitization by dyes and self-photo-sensitized process. Thus, insignificant photocatalytic activity may be caused by the inability of photo-excited electron of MO to transfer to the conduction band (CB) of Degussa P25.

The Ag, S co-doped $TiO_2$ exhibited higher photocatalytic activity regardless the calcination temperature applied in comparison to S-doped $TiO_2$ and commercial Degussa P25 under identical experimental conditions showing a promotional effect of the simultaneous co-doping (FIG. 8). Also, doping with $Ag^+$ ions effectively suppressed the recombination of the photogenerated charge-carriers on the surface of the catalyst, therefore a larger number of molecules was adsorbed and subsequently oxidized.

The increase in calcination temperature from 450° C. to 700° C. demonstrated nearly 20% increase in MO degradation efficiency obtained in 3 h in comparison to 4 h, which were necessary to degrade 88% of MO in the presence of Ag, S-codoped $TiO_2$ nanophotocatalyst. It may be explained by the so called 'critical crystallite size', which limits the photocatalytic activity of as-prepared nanocatalysts. When the surface of $TiO_2$ is irradiated, the electron-hole pair is created due to the ejection of an electron ($e^-$) from the valence band (VB), subsequently leaving the hole ($h^+$) in the VB. According to Baiju and co-workers, generated $e^-/h^+$ pair migrates to the particle surface, e.g. conduction band (CB), however if the tallite size is too large, the travel distance for the pair increases, thus more opportunities to recombine occur. However, when the crystallite size is small, the $e^-/h^+$ pair may get trapped at the active surface sites before even surface charge recombination process is initiated. In addition, critical crystallite size may also take place due to the kinetic effects. For instance, the activation energy is directly related to the particle size, which varies with changes in temperature, because a change in temperature can significantly alter the kinetic energy of atoms in anatase phase. Therefore, the optimum reported crystallite size was reported to be ~15 nm.

Increased photocatalytic activity could be attributed to i) the high stability and crystallization degree of doped anatase, which facilitated the transfer of electrons and thus decreased their recombination within the photogenerated holes, and/or ii) doping generated more oxygen vacancies or distortions leading to the lattice defects that could capture the photoinduced electrons inhibiting the recombination of electrons and holes.

TABLE 1

Selected parameters for various catalysts

| | Dp, nm | ε | βcosθ | sinθ | FWHM, 2°θ | MO % Degradation | Reaction rate, $min^{-1}$ |
|---|---|---|---|---|---|---|---|
| Ag, S co-doped $TiO_2$, 450° C. | 9.6 | 0.47 | 0.0144 | 0.015 | 0.89 | 88 | $8.5 \times 10^{-3}$ |
| Ag, S co-doped $TiO_2$, ~700° C. | 14.4 | 0.31 | 0.0096 | 0.015 | 0.59 | 98 | $19.4 \times 10^{-3}$ |
| S-doped $TiO_2$, 450° C. | 20.5 | 0.22 | 0.0068 | 0.015 | 0.41 | 70 | $1.6 \times 10^{-3}$ |
| Degussa P25 | 21.2 | 0.21 | 0.0066 | 0.015 | 0.39 | 12 | $5.3 \times 10^{-4}$ |

The use of silver and garlic as the doping agent resulted in enhanced photocatalytic activity as compared to single dopants used alone. Also, higher calcination temperatures were used yet the titanium dioxide remained in the anatase phase and also resulted in preferred size nanocrystals. Similar calcination methods not using a dopant or using a single dopant (such as guanidine nitrate) resulted in the formation of titanium dioxide in the rutile phase and larger nanocrystals.

MO was efficiently degraded in the presence of visible light activated Ag, S co-doped $TiO_2$ and S-doped $TiO_2$ nanocatalysts with degradation efficiencies from 70 to 100% and the reaction rate constants ranging from $1.6\times10^{-3}$ to $19.4\times10^{-3}$ $min^{-1}$.

EXAMPLE 15

Synthesis of a Titanium Dioxide Photocatalyst Using Microcrystalline Cellulose

During a typical sol-gel synthesis of $TiO_2$/MC nanocomposites at room temperature, 20 g $Ti^{4+}$ salt (digested to 50% in HCl) was taken in 1000 mL of water. Then 20 g of microcrystalline cellulose (MC) was added to the solution and the content magnetically stirred for 30 min. Ammonium hydroxide solution was used to increase the pH to 9. Subsequently, the solution was stirred at room temperature for 24 hours. The product was dried at 60° C. overnight, crushed in the mortar and calcined at 350° C. in air for 2 hours.

EXAMPLE 16

Analysis of the Effectiveness of the Catalyst by Degradation of Methylene Blue (MB)

Photo-bleaching and adsorption of MB onto $TiO_2$/MC and Degussa P25 The adsorption of MB was evaluated in a static batch experiment in the dark. Aqueous solution of 100 mg $L^{-1}$ MB was magnetically stirred for 135 min in the presence of 3 g $L^{-1}$ nanocomposite and Degussa P25. The supernatant liquid was filtered and the equilibrium as well as time-dependant concentration of dye was determined using UV vis spectrophotometer.

The photocatalytic activity of as-prepared nanocomposites were examined by the photo-bleaching experiments using MB dye as a model compound, because it has a good resistance to light degradation and a well defined optical absorption maximum in the visible light range.

The typical photo-bleaching of MB was performed at a room temperature (25±1° C.) in 20 mL quartz photochemical reactor with 3 g L$^{-1}$ as-prepared catalyst and 100 mg L$^{-1}$ of MB aqueous solution. The photo-reactor was equipped with a magnetic stirrer and surrounded with water-jacket for the adequate temperature control. All the UV irradiation with the wavelength less than 420 nm was removed by the cutoff glass/water filter. The photocatalytic reactor along with the light source was positioned into the black metal box to prevent the light leakage. The reaction suspension was irradiated with 300 W metal halogen desk lamp located approx. 15 cm away from the system. Concentration of MB in the solution was measured every 60 min for 4 hours, unless specified otherwise. At regular intervals, approx 3 mL of aliquots was withdrawn from the solution, passed through a 0.45 μm syringe filter and analyzed by a UV-vis spectrophotometer (Hewlett Packard 845X) at the characteristic wavelength (664 nm) to determine the MB photo-bleaching efficiency using earlier established calibration curve.

The rate of MB degradation was assumed to obey pseudo-first order reaction kinetics and, therefore, the photo-degradation rate constant, k (min$^{-1}$) was obtained according to the power rate law:

$$-\frac{d[C]}{dt} = k[C] \tag{2}$$

This equation may be further integrated to:

$$-\ln\left(\frac{C}{C_o}\right) = kt \tag{3}$$

$$[C] = [C]_o e^{-kt} \tag{4}$$

where $C_o$ and $C$ are the initial and time related MB concentration, respectively ((mg L$^{-1}$), t is time (min) and k is the pseudo-first order reaction rate constant (min$^{-1}$).

Figure 9A:
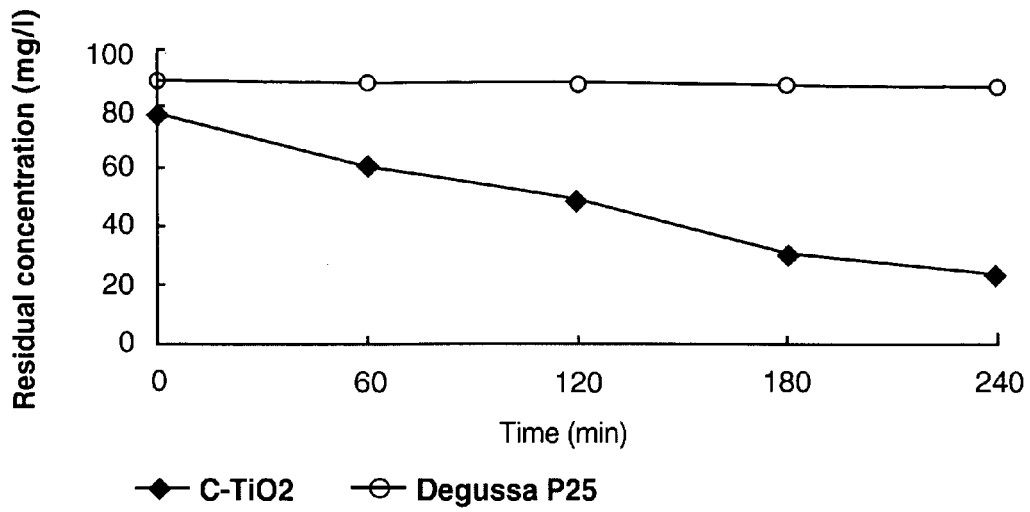
FIG. 9a shows the kinetics of MB photobleaching in the presence of $TiO_2$/MC and Degussa P25 catalysts.
Figure 9B:
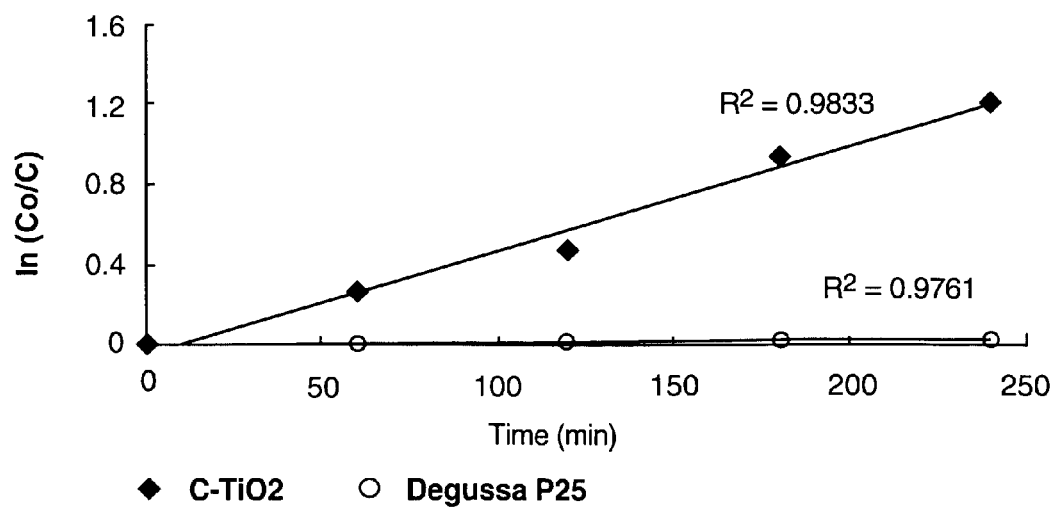
FIG. 9b shows the logarithmic dependence of MB photobleaching with the visible light irradiation on the $TiO_2$/MC and Degussa P25 catalysts.

Kinetics of MB Photo-Bleaching:

Photo-bleaching of MB was evaluated in the presence of the visible light. Initially, the MB solution was stirred in the dark for 30 min to establish the adsorption-desorption equilibrium conditions and then visible light irradiation was initiated. FIGS. 9a and 9b shows the kinetics of MB photo-bleaching with an initial concentration of 78 mg L$^{-1}$, which was adjusted from the initial concentration before the adsorption process, in the presence of TiO$_2$/MC and Degussa P25 catalysts. To assess the effect of direct photolysis without the addition of catalyst, the MB solution was irradiated for 4 hours. Negligible amount of dyes degradation (~3-5%) may be attributed to the self-sensitization of the dye molecule in the presence of the visible light. However, as this amount was insignificant, direct photolysis effect on the overall degradation of MB was neglected.

The slope in FIG. 9a is consistent with the first reaction order kinetics as confirmed by the linear transform ln(C$_o$/C) =f(t) and presented in FIG. 9b. For a first-order reaction, the rate of reaction was directly proportional to the concentration of MB and was 5.02×10$^{-3}$ and 5.3×10$^4$ min$^{-1}$ for TiO$_2$/MC and Degussa P25, respectively.

When the solution is irradiated with visible light, the electron is injected from the excited dye molecule adsorbed on the catalyst surface into the conduction band of the TiO$_2$[8]:

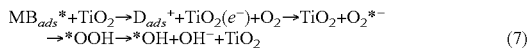

$$\text{MB}_{ads}^* + \text{TiO}_2 \rightarrow \text{D}_{ads}^+ + \text{TiO}_2(e^-) + \text{O}_2 \rightarrow \text{TiO}_2 + \text{O}_2^{*-} \rightarrow ^*\text{OOH} \rightarrow ^*\text{OH} + \text{OH}^- + \text{TiO}_2 \tag{7}$$

Thus, the electron that is trapped by the molecular oxygen present on the TiO$_2$ surface generates highly active radicals that are responsible for the photo-bleaching of MB molecules.

EXAMPLE 17

Properties of the Photocatalyst Formed by Example 15

The X-ray diffraction (XRD) patterns of as-prepared nanocomposites and commercially available Degussa P25 were recorded on a X'Pert Pro MPD X-ray diffractometer with a Cu Kα source and diffraction angle range of 2θ=10-80° with a count time of 20 s at each point. The accelerating voltage and applied current were 45 kV and 40 mA, respectively. The average crystallite size (Dp) was calculated as a function of the peak width according to the Scherrer's equation:

$$Dp = \frac{0.9\lambda}{\beta \cos\theta} \tag{1}$$

where Dp is the crystallite size (nm), λ is X-ray wavelength (0.154056 nm), θ is the Bragg angle and β is full width at half maximum (FWHM). FWHM of each diffraction line was determined from the profile measured with a scanning rate of ½° (2θ) min$^{-1}$, which was calibrated by standard silicon powder for instrumental broadening. The phases were identified by using Joint Committee on Powder Diffraction Standards (JCPDS).

The morphology of samples was evaluated with the means of electron scanning microscopy (FEI XL 30 ESEM) equipped with EDS (energy dispersive X-ray spectroscopy) operating at 15-20 kV on gold-sputtered samples. Transmission electron microscopic (TEM) images were recorded using FEI CM20 TEM operating at an accelerated voltage of 60-120 keV. Prior to the analysis, the samples were dispersed in ethanol by an ultrasonic irradiation for 20 min and a drop of the suspension was directly deposited onto air dried lacey carbon coated copper grid. The thermogravimetric analysis (TGA) was performed using TGA Q5000 (TA instruments) analyzer with a heating rate of 10 degrees/min in an air flow adopting a ramp method (temperature increase from 100 to 800° C.).

The XRD patterns of as-prepared nanocomposite and Degussa P25 show relatively broad peaks characteristics indicate the high degree of crystallinity with mean Dp of 17.3 nm, which is quite similar to the crystallite size of Degussa P25 (21.2 nm), therefore suggesting that the dimension of the TiO$_2$ particles did not grow in the presence of cellulose.

The XRD patterns indicated that nanocomposites were dominated by the characteristic peaks of anatase (tetragonal, a=b=3.78 Å; c=9.50 Å) with minor traces of rutile (tetragonal, a=b=4.58 Å; c=2.95 Å). The strongest peaks observed in the nanocomposite sample corresponded to anatase (101, 004, 200 planes) at 2θ=25.3°, 37.8° and 48.4°, respectively. The trace rutile phase (110 plane) was observed at 2θ=27.4°. The reason for the insignificant formation of rutile phase at 350° C. may be that anatase linear chains are linked together only through octahedron edges. Thus, the anatase phase is more likely to form at higher temperatures where more collision among molecules is statistically favorable due to the availability of edges to form a bond.

In addition, residue of cellulose characteristic peak was observed at 2θ=23° (JCPDS 03-0289); some small peaks at 2θ=27.1° and 38.3° indicate modification of the crystal planes in cellulose.

Figure 11:
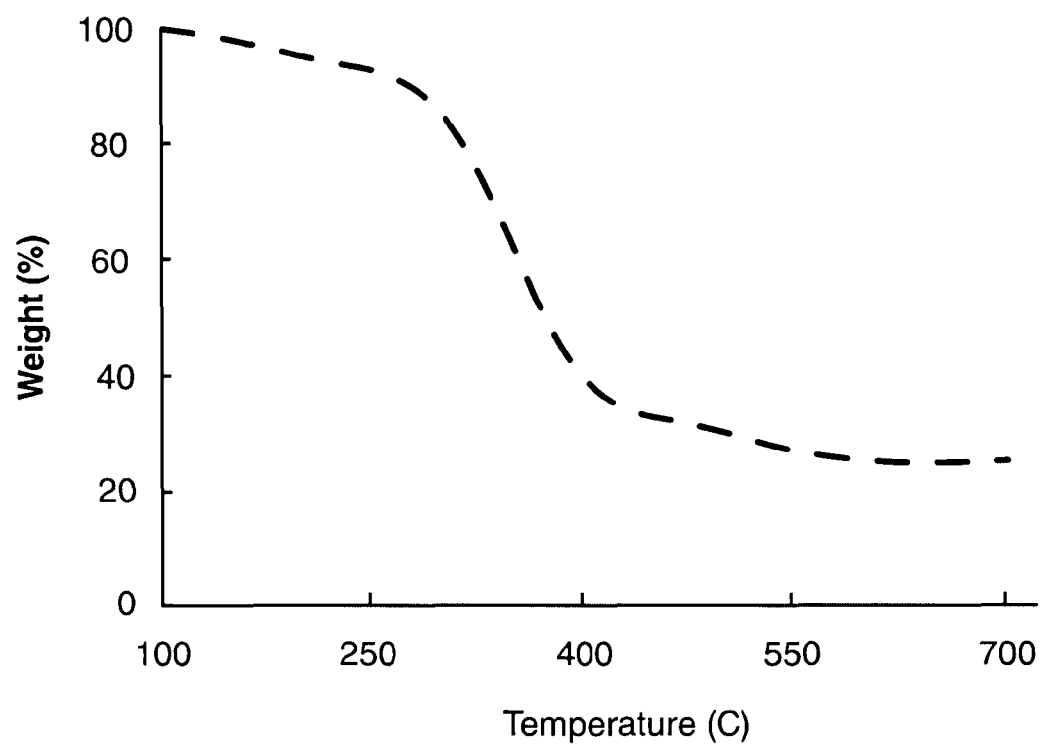
FIG. 11 shows the thermogravimetric curve of $TiO_2$/MC nanocomposite.

Thermal Analysis:

Thermal degradation pattern of TiO$_2$/MC is shown in FIG. 11. An insignificant weight loss below 120° C. may be assigned to the evaporation of water from the samples and primary oxidation of cellulose.[3] The weight loss between 120° C. and 300° C. is attributed to the oxidation and carbonization of the MC without interacting with TiO$_2$.[7] It may also be ascribed to the removal of residual organics from the titania.[4] The highest weight loss was observed in the temperature range of 300-550° C., which is attributed to the decomposition of cellulose.

Morphology of the Nanocomposites:

A SEM image analysis of TiO$_2$/MC nanocomposite revealed a nearly homogeneous distribution and incorporation of TiO$_2$ at the MC surface indicating some miscibility between MC and TiO$_2$ particles.[3] It is evident that experimental and reaction conditions did not alter the structure of the nanocomposite and TiO$_2$ nanoparticles were strongly attached to the cellulosic fibers due to very strong electrostatic or chemical interactions between the TiO$_2$ nanoparticles and polysaccharides of the MC fibers. Marques and colleagues (2006) explained these interactions as hydroxyl groups in anhydroglucose or the carboxyls in uronic acid moieties acting as nucleation initiators to promote the development of TiO$_2$ nanoparticles.

EDS-pattern of TiO$_2$/MC nanocomposite may be seen in FIG. 3b. There are twelve peaks associated with C Kα, Ti Kα, V Kα, O Kα, Ga Kα and Au Kα. However, lines of V Kα, Ga Kα and Au Kα are either constituents of the grid used for the analysis or impurities. According to FIG. 3b, O, C and Ti correspond to the nanocomposites prepared by the synthesis protocol. Peaks around 0.2-0.3 keV, which is TiO$_2$ surface and an intense peak at about 4.5 keV, which is assigned to TiO$_2$ in the bulk form.

A TEM image of TiO$_2$/MC nanocomposite shows nearly spherical aggregates stabilized by the presence of MC of about 10-20 nm with narrow particle size distribution were observed, which is consistent with XRD findings.

Figure 10:
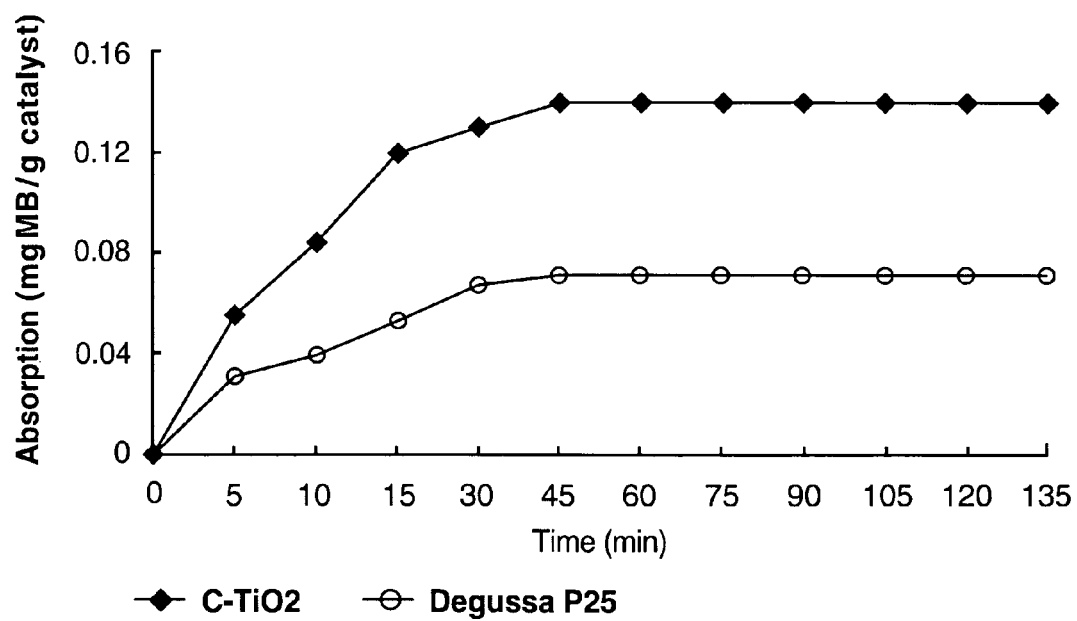
FIG. 10 shows the adsorption of MB in the absence of visible light (V=0.02 L, $C_o$=98.5 mg $L^{-1}$, m=3 g $L^{-1}$)

Adsorption of Methylene Blue on TiO$_2$/MC Nanocomposite:

Methylene blue (MB) has been selected in the adsorption study, owing to its widespread applications, adsorbtivity by the most surfaces in the form of ionic micelles and representative properties as a medium sized adsorbed molecule of pore size >13 Å. Therefore, to evaluate the adsorption of MB onto the nanocomposite and commercially available Degussa P25, the reaction was executed in the dark. FIG. 10 shows the adsorption of MB (initial concentration of 98.5 mg L$^{-1}$) as a function of time over TiO$_2$/MC and Degussa P25. It is evident that more than 90% of adsorption occurred within initial half an hour. Degussa P25 showed negligible adsorption (less than 10%), whereas MB adsorption onto TiO$_2$/MC nanocomposite was nearly 20%, which reached equilibrium after 30 min of stirring the reaction mixture in the dark.

The quantity of adsorbed MB per unit mass of the catalyst is calculated as:

$$Q_t = \frac{V \times (C_o - C_t)}{m} \quad (5)$$

where $Q_t$ is the adsorption capacity (mg MB/g of the catalyst), $C_o$ and $C_t$ are the initial and concentrations of MB (mg L$^{-1}$), V is volume of the solution (L) and m is the weight of the catalyst (g).

The isotherm was a typical Type I, indicating that the catalysts were microporous.[11] In this case, the uptake of MB molecules was initially fast until the surface coverage was saturated and the interactions between the adsorbed and free molecules ceased to dominate the process. Therefore, one of the adsorption driving forces was the increased concentration gradient between the dye in the solution and on the TiO$_2$/MC surface.

The explanation of MB adsorption onto nanocomposite and commercially available Degussa P25 catalyst is proposed. It is reported that the negatively charged solids improve the adsorption of various cationic species such as methylene blue. The point of zero charge of Degussa P25 is at pH 6.8, suggesting that TiO$_2$ surface is positively charged at pH<6.8, whereas negatively charged at pH>6.8. Moreover, higher pH reduces the electrostatic repulsion between MB cation and the adsorption sites, therefore increasing the adsorption capacity. The pH of the reaction mixture was about 7-8, thus the surface of as-prepared catalysts was negatively charged:

$$TiOH + OH^- \rightarrow TiO^- + H_2O \quad (6)$$

The quantity of adsorbed MB on TiO$_2$/MC and Degussa P25 at equilibrium was only 0.14 and 0.071 mg of MB/g of the catalyst, respectively.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

What is claimed is:

1. A method for preparing a doped titanium dioxide photocatalyst comprising;
   contacting a non-oxide titanium salt with a dopant and allowing them to react,
   forming an insoluble non-oxide intermediate, and
   heating the insoluble non-oxide intermediate to form the doped titanium dioxide photocatalyst,
   wherein the photocatalyst has photocatalytic activity toward organic compounds under visible light.

2. The method of claim 1 wherein the photocatalyst is heated at a sufficient temperature and sufficient time to form anatase phase titanium dioxide with only traces of rutile or brookite phases.

3. The method of claim 1 wherein the dopant contains at least one organic compound and at least one inorganic compound and atoms from each compound are retained in the photocatalyst.

4. The method of claim 1 wherein the dopant contains a polymer.

5. The method of claim 1 the dopant contains a mixture of plural organic compounds.

6. The method of claim 1 wherein the photocatalyst is composed of crystals having a size of 10 to about 20 nm.

7. The method of claim 1 wherein the photocatalyst has a BET surface area of >150 m²/gram.

8. The method of claim 3 wherein the dopant contains silver, copper or bismuth metal atoms or ions.

9. The method of claim 1 wherein the dopant contains both an organic compound or ion and an inorganic compound.

10. The method of claim 1 wherein the visible light capable of photocatalyzing organic compounds does not include ultraviolet light.

11. The method of claim 10 wherein the visible light capable of photocatalyzing organic compounds is greater than 420 nm.

12. A doped anatase phase titanium dioxide photocatalyst capable of photocatalyzing organic compounds under visible light prepared by:
    contacting a non-oxide titanium salt with a dopant and allowing them to react,
    forming an insoluble non-oxide intermediate, and
    heating the insoluble non-oxide intermediate to form the doped titanium dioxide photocatalyst,
    wherein the anatase phase titanium dioxide photocatalyst contains at most traces of rutile or brookite phases.

13. The photocatalyst of claim 12 wherein the dopant contains at least one organic compound and at least one inorganic compound and atoms from each compound are retained in the photocatalyst.

14. The photocatalyst of claim 12 wherein the dopant contains a polymer.

15. The photocatalyst of claim 12 the dopant contains a mixture of plural organic compounds.

16. The doped titanium dioxide catalyst of claim 12 wherein the dopant contains nitrogen or sulfur atoms or ions.

17. The doped titanium dioxide catalyst of claim 16 wherein the dopant contains guanidine or a salt thereof.

18. The doped titanium dioxide catalyst of claim 12 wherein the dopant contains both an organic compound or ion and an inorganic compound.

19. The doped titanium dioxide catalyst of claim 12 wherein the visible light capable of photocatalyzing organic compounds does not include ultraviolet light.

20. The doped titanium dioxide catalyst of claim 19 wherein the visible light photocatalyzing organic compounds is greater than 420 nm.

\* \* \* \* \*